United States Patent
Tanaka et al.

(10) Patent No.: US 10,111,890 B2
(45) Date of Patent: Oct. 30, 2018

(54) 9-AMINOMETHYL MINOCYCLINE COMPOUNDS AND USES THEREOF

(71) Applicant: Paratek Pharmaceuticals, Inc., Boston, MA (US)

(72) Inventors: S. Ken Tanaka, Bellevue, WA (US); Evangelos L. Tzanis, Newtown Square, PA (US); Lynne Garrity-Ryan, Melrose, MA (US); Amy L. Manley, Phoenixville, PA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 15/667,683

(22) Filed: Aug. 3, 2017

(65) Prior Publication Data

US 2018/0055859 A1 Mar. 1, 2018

Related U.S. Application Data

(60) Provisional application No. 62/532,454, filed on Jul. 14, 2017, provisional application No. 62/514,479, filed on Jun. 2, 2017, provisional application No. 62/370,527, filed on Aug. 3, 2016.

(51) Int. Cl.
*A61K 31/65* (2006.01)
*A61K 9/00* (2006.01)

(52) U.S. Cl.
CPC ............ *A61K 31/65* (2013.01); *A61K 9/0053* (2013.01)

(58) Field of Classification Search
None
See application file for complete search history.

(56) References Cited

U.S. PATENT DOCUMENTS

| | | | |
|---|---|---|---|
| 2009/0253660 A1* | 10/2009 | Johnston | A61K 31/65 514/152 |
| 2014/0005420 A1* | 1/2014 | Cvetovich | C07C 237/26 552/205 |
| 2015/0087711 A1* | 3/2015 | Johnston | A61K 31/65 514/619 |

OTHER PUBLICATIONS

Noel et al., Antimicrobial Agents and Chemotherapy p. 5650-5654.*
Database Caplus Chemical Abstracts Service, Columbus, Ohio, US; Database Accession No. 2009:581285, Abstract of Wang et al., Drugs of the Future (2009), 34(1), 11-15.*
Levison et al., "Pharmacokinetics and Pharmacodynamics of Antibacterial Agents." Infectious disease clinics of North America 23.4 (2009): 791—vii. PMC. Web. Feb. 2, 2018.*
International Search Report and Written Opinion for PCT/US17/45220 dated Oct. 12, 2017 pp. 1-17.

* cited by examiner

*Primary Examiner* — Karl J Puttlitz
(74) *Attorney, Agent, or Firm* — McCarter & English, LLP; Elizabeth A. Hanley; Yu Lu

(57) ABSTRACT

Methods and compositions for using a tetracycline compound to treat bacterial infections are described. In one embodiment, for example, the invention provides a method of treating a subject for an infection, comprising administering to said subject an effective amount of 9-[(2,2-dimethyl-propyl amino)-methyl]-minocycline or a salt thereof, such that said subject is treated, wherein the 9-[(2,2-dimethyl-propyl amino)-methyl]-minocycline is administered orally at a dose of about 450 mg per day for two consecutive days, then at a dose of about 300 mg per day for 5 or more days.

17 Claims, 6 Drawing Sheets

9-AMINOMETHYL MINOCYCLINE COMPOUNDS AND USES THEREOF

REFERENCE TO RELATED APPLICATIONS

This application claims the benefit of the filing date under 35 U.S.C. § 119(e) to U.S. Provisional Application No. 62/370,527, filed on Aug. 3, 2016; 62/514,479, filed on Jun. 2, 2017; and 62/532,454, filed on Jul. 14, 2017, the entire contents of each of which is incorporated herein by reference.

BACKGROUND OF THE INVENTION

The development of the tetracycline antibiotics was the direct result of a systematic screening of soil specimens collected from many parts of the world for evidence of microorganisms capable of producing bactericidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of minocycline compounds, without the ring-attached methyl group present in earlier tetracyclines, was prepared in 1957 and became publicly available in 1967; and minocycline was in use by 1972.

Later research efforts have focused on developing new tetracycline antibiotic compositions effective under varying therapeutic conditions and routes of administration. New tetracycline analogues have also been investigated which may prove to be equal to or more effective than the originally introduced minocycline compounds. Examples include U.S. Pat. Nos. 2,980,584; 2,990,331; 3,062,717; 3,165,531; 3,454,697; 3,557,280; 3,674,859; 3,957,980; 4,018,889; 4,024,272; and 4,126,680. These patents are representative of the range of pharmaceutically active tetracycline and tetracycline analogue compositions.

Historically, soon after their initial development and introduction, the tetracyclines were found to be highly effective pharmacologically against *rickettsia*; a number of Gram-positive and Gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes.

However, this widespread use of tetracyclines for both major and minor illnesses and diseases led directly to the emergence of resistance to these antibiotics even among highly susceptible bacterial species both commensal and pathogenic (e.g., *pneumococci* and *Salmonella*). The rise of tetracycline-resistant organisms has resulted in a general decline in use of tetracyclines and tetracycline analogue compositions as antibiotics of choice. In addition, other antibacterial agents have also been over used, creating strains of multiple drug resistant (MDR) bacteria.

Over the past decade, Gram-positive bacteria with multi-drug resistance to a diverse range of antibiotics have emerged as a major treatment challenge. Two developments raise the specter that currently available antibiotics may become even less useful for treatment of infections caused by Gram-positive organisms. The first is the emergence of vancomycin resistance in *Enterococcus* species (spp.) and the subsequent transfer of those resistance elements to *Staphylococcus aureus*. Although vancomycin-resistant *Staphylococcus aureus* have not become epidemiologically significant, their very existence raises concern because vancomycin has been the agent of choice for infections caused by resistant Gram-positive pathogens.

The second important development is the appearance of community-acquired methicillin-resistant *Staphylococcus aureus* (MRSA). These strains are increasingly becoming multi-drug resistant over time. In many areas of the world, MRSA infections represent the majority of sporadic staphylococcal infections with community-onset. These strains also have been associated with numerous outbreaks of localized (skin and skin structure) and invasive (bacteremic) infections.

Other than the general need for effective antibacterial agents for the treatment of bacterial infections, there is also a specific need for oral antibiotic therapies.

Compared to IV administration, oral antibiotic therapies can be advantageous because they can eliminate the requirement for hospital visit and/or stay, thus reducing the overall cost of treatment, limiting a patient's exposure to secondary infection in the hospital setting, and increasing the availability of the treatment in areas where hospitals are less accessible or unavailable, particularly in the remote or economically underdeveloped areas or parts of the world.

Unfortunately, due to the rise of antibiotic resistance, use of older agents has led to increasing hospital visits, which in turn increases patients' chances of becoming infected by other bacteria.

Thus there is still a need for a new, effective oral antibacterial agent, particularly oral only dosing regimens, for treating, for example, a bacterial skin or skin structure infection, such as ABSSSI. ABSSSI alone is responsible for more than 750,000 hospitalizations per year (based on the latest data in 2011), representing a 17.3% increase in hospitalized ABSSSI patients from 2005-2011.

SUMMARY OF THE INVENTION

One aspect of the invention provides a method of treating a human subject in need of treatment for a bacterial skin or skin structure infection, comprising orally administering to the subject an effective amount of 9-[(2,2-dimethyl-propyl amino)-methyl]-minocycline (also known as Omadacycline or OMC) or a salt thereof, such that the subject is treated, wherein the 9-[(2,2-dimethyl-propyl amino)-methyl]-minocycline is administered as once-daily oral dose of 450 mg or 600 mg for 5 or more days.

In certain embodiments, the once-daily oral dose is 450 mg, administered for 5 or more consecutive days.

In certain embodiments, the once-daily oral dose is 600 mg, administered for 5 or more consecutive days.

A related aspect of the invention provides a method of treating a human subject in need of treatment for a bacterial skin or skin structure infection, comprising orally administering to the subject an effective amount of 9-[(2,2-dimethyl-propyl amino)-methyl]-minocycline or a salt thereof, such that the subject is treated, wherein the 9-[(2,2-dimethyl-propyl amino)-methyl]-minocycline is administered as once-daily oral dose of 300 mg, for 5, 6, 7, or 8 consecutive days.

Another related aspect of the invention provides a method of treating a human subject in need of treatment for a bacterial skin or skin structure infection, comprising orally administering to the subject an effective amount of 9-[(2,2- dimethyl-propyl amino)-methyl]-minocycline or a salt thereof, such that the subject is treated, wherein the 9-[(2,2-dimethyl-propyl amino)-methyl]-minocycline is administered with an oral loading dose, followed by once-daily oral doses of 300-600 mg (e.g., 300 mg, 450 mg, or 600 mg) for 5 or more days.

In certain embodiments, the oral loading dose consists essentially of/consists of one oral dose of 600 mg of the 9-[(2,2-dimethyl-propyl amino)-methyl]-minocycline, administered 24 hours before the first of the once-daily oral doses of 300 mg, 450 mg, or 600 mg.

In certain embodiments, the oral loading dose consists essentially of/consists of one oral dose of 450 mg of the 9-[(2,2-dimethyl-propyl amino)-methyl]-minocycline, administered 24 hours before the first of the once-daily oral doses of 300 mg, 450 mg, or 600 mg.

In certain embodiments, the oral loading dose consists essentially of/consists of two oral doses of 300 mg of the 9-[(2,2-dimethyl-propyl amino)-methyl]-minocycline, administered 12 hours and 24 hours, respectively, before the first of the once-daily oral doses of 300 mg, 450 mg, or 600 mg.

In certain embodiments, the oral loading dose consists essentially of/consists of two oral doses of 450 mg of the 9-[(2,2-dimethyl-propyl amino)-methyl]-minocycline, administered 12 hours and 24 hours, respectively, before the first of the once-daily oral doses of 300 mg, 450 mg, or 600 mg.

In certain embodiments, the oral loading dose consists essentially of/consists of two oral dose of 600 mg of the 9-[(2,2-dimethyl-propyl amino)-methyl]-minocycline, administered 24 hours and 48 hours, respectively, before the first of the once-daily oral doses of 300 mg, 450 mg, or 600 mg.

In certain embodiments, the oral loading dose consists essentially of/consists of two oral dose of 450 mg of the 9-[(2,2-dimethyl-propyl amino)-methyl]-minocycline, administered 24 hours and 48 hours, respectively, before the first of the once-daily oral doses of 300 mg, 450 mg, or 600 mg.

In another aspect, the invention provides a method of treating a human subject in need of treatment for a bacterial skin or skin structure infection, comprising orally administering to the subject an effective amount of 9-[(2,2-dimethyl-propyl amino)-methyl]-minocycline or a salt thereof, such that the subject is treated, wherein the 9-[(2,2-dimethyl-propyl amino)-methyl]-minocycline is administered orally at a dose of about 450 mg per day for two consecutive days, then at a dose of about 300 mg per day for 5 or more days.

In certain embodiments, the bacterial skin or skin structure infection is wound infection, cellulitis/erysipelas, major abscess, furuncles/boils, carbuncle, Staphylococcal scalded skin syndrome (SSSS), or ecthyma.

In certain embodiments, the bacterial skin or skin structure infection is Acute Bacterial Skin and Skin Structure Infection (ABSSSI), such as community-acquired ABSSSI.

In certain embodiments, the ABSSSI is greater than or equal to 75 cm$^2$ in total surface area of contiguous involved tissue.

In certain embodiments, he ABSSSI comprises wound infection, cellulitis/erysipelas, and/or major abscess.

In certain embodiments, the bacterial skin or skin structure infection is a result of skin injury including but not limited to trauma, a surgical procedure, or IV drug use.

In certain embodiments, the bacterial skin or skin structure infection is a result of vascular insufficiency or edema.

In certain embodiments, the human subject is administered 9-[(2,2-dimethyl-propyl amino)-methyl]-minocycline under fasting condition.

In certain embodiments, the 9-[(2,2-dimethyl-propyl amino)-methyl]-minocycline is administered once per day (e.g., each oral dose is administered about 24 hours apart).

In certain embodiments, the subject is treated up to and including about 14 days, up to and including about 10 days, up to and including about 9 days, up to and including about 8 days, or up to and including about 7 days, up to and including about 5 days, such that the subject is treated.

In certain embodiments, the subject is treated for 7-10 days.

In certain embodiments, the subject is treated for 8 days.

In certain embodiments, the salt is a tosylate salt.

In certain embodiments, the bacterial skin or skin structure infection is known or suspected to be caused by Gram-positive pathogens. For example, the Gram-positive pathogens may include *Staphylococcus aureus, Staphylococcus lugdunensis, Streptococcus species, Streptococcus agalactiae, Streptococcus mitis, Enterococcus* species (*Enterococcus faecalis* (such as VRE or VSE), or *Enterococcus faecium* (such as VRE or VSE)), *Streptococcus anginosus* group (*S. anginosus, S. constellatus*, and *S. intermedius*, that is beta-, alpha- or non-hemolytic), *Viridans* group Streptococci (VGS), *Clostridium perfringens, Finegoldia magna*, or a combination thereof. The *Staphylococcus aureus* may be methicillin-resistant *Staphylococcus aureus* (MRSA), or methicillin-susceptible *Staphylococcus aureus* (MSSA). The *Streptococcus* species may include *Streptococcus anginosus* group. The *Streptococcus* species may include beta-hemolytic Streptococci or *S. anginosus*. The *Streptococcus* species may include non-hemolytic Streptococci or *S. intermedius*. The *Streptococcus* species may include alpha-hemolytic Streptococci or *S. constellatus*. The *Enterococcus* species may include *Enterococcus faecalis* (VSE). The *Streptococcus* species may include *Streptococcus pyogenes*.

In certain embodiments, the bacterial skin or skin structure infection is known or suspected to be caused by Gram-negative pathogens. For example, the Gram-negative pathogens may include *Enterobacter cloacae, Escherichia coli, Klebsiella pneumoniae, Prevotella denticola, Prevotella melaninogenica*, or a combination thereof.

In certain embodiments, the bacterial skin or skin structure infection is known or suspected to be caused by any of the preceding Gram-positive and Gram-negative pathogens, or a combination thereof.

In certain embodiments, gastrointestinal (GI) adverse events (AEs) associated with treatment are predominantly mild. In certain embodiments, GI adverse events (AEs) associated with treatment do not result in discontinuation of therapy.

In certain embodiments, $AUC_{0-24}$ after the first two doses of 9-[(2,2-dimethyl-propyl amino)-methyl]-minocycline or a salt thereof is about 10,000 ng*h/mL.

In certain embodiments, each dose of the 9-[(2,2-dimethyl-propyl amino)-methyl]-minocycline or salt thereof is administered as 150 mg tablets.

In certain embodiments, the method has a clinical success rate of about 70-100%. For example, the clinical success rate may be about 80-100%, about 79-98%, about 79-94%, about 84-98%, about 80-88%, or about 84-89%.

In certain embodiments, the clinical success rate is observed at 48-72 hours after the first oral dose, and is about 79-94%, or about 84-89%, or about 87.5%. In certain embodiments, the ABSSSI consists essentially of wound infection, and the clinical success rate is about 84-94%, or about 89%. In certain embodiments, the ABSSSI consists essentially of cellulitis/erysipelas, and the clinical success rate is about 74-84%, or about 79%. In certain embodiments, the ABSSSI consists essentially of major abscess, and the clinical success rate is about 90-98%, or about 94%.

In certain embodiments, the clinical success rate is overall clinical success rate observed at about 7-14 days after the last dose of treatment, and is about 79-98%, about 75-95%, about 79-89%, 84%, about 95-100%, or about 98%. In certain embodiments, the ABSSSI consists essentially of wound infection, and the overall clinical success rate is about 80-85%, or is about 82-83%. In certain embodiments, the ABSSSI consists essentially of cellulitis/erysipelas, and the overall clinical success rate is about 85-91%, about 87-88%, or is about 88%. In certain embodiments, the ABSSSI consists essentially of major abscess, and the overall clinical success rate is about 80-88%, or about 84%.

In a related aspect, the invention provides a method of treating a human subject in need of treatment for a bacterial skin or skin structure infection, comprising administering to the subject an effective amount of 9-[(2,2-dimethyl-propyl amino)-methyl]-minocycline or a salt thereof, such that the subject is treated, wherein the 9-[(2,2-dimethyl-propyl amino)-methyl]-minocycline is administered intravenously (i.v.) at a dose of about 150 mg per day for two consecutive days, then at a dose of about 300 mg per day orally for 5 or more days. Because of the known bioequivalence established between oral and i.v. doses for 9-[(2,2-dimethyl-propyl amino)-methyl]-minocycline, the 150 mg i.v. dose is considered bioequivalence of 450 mg oral dose. Thus the alternative embodiment in this aspect of the invention is considered to be encompassed within the scope of the instant invention.

It should be understood that any one embodiment can be combined with any one or more other embodiments, including those disclosed only in the examples or only under one aspect of the invention, unless the combination is inappropriate or expressly disclaimed.

DETAILED DESCRIPTION OF THE INVENTION

1. Overview

Figure 1:
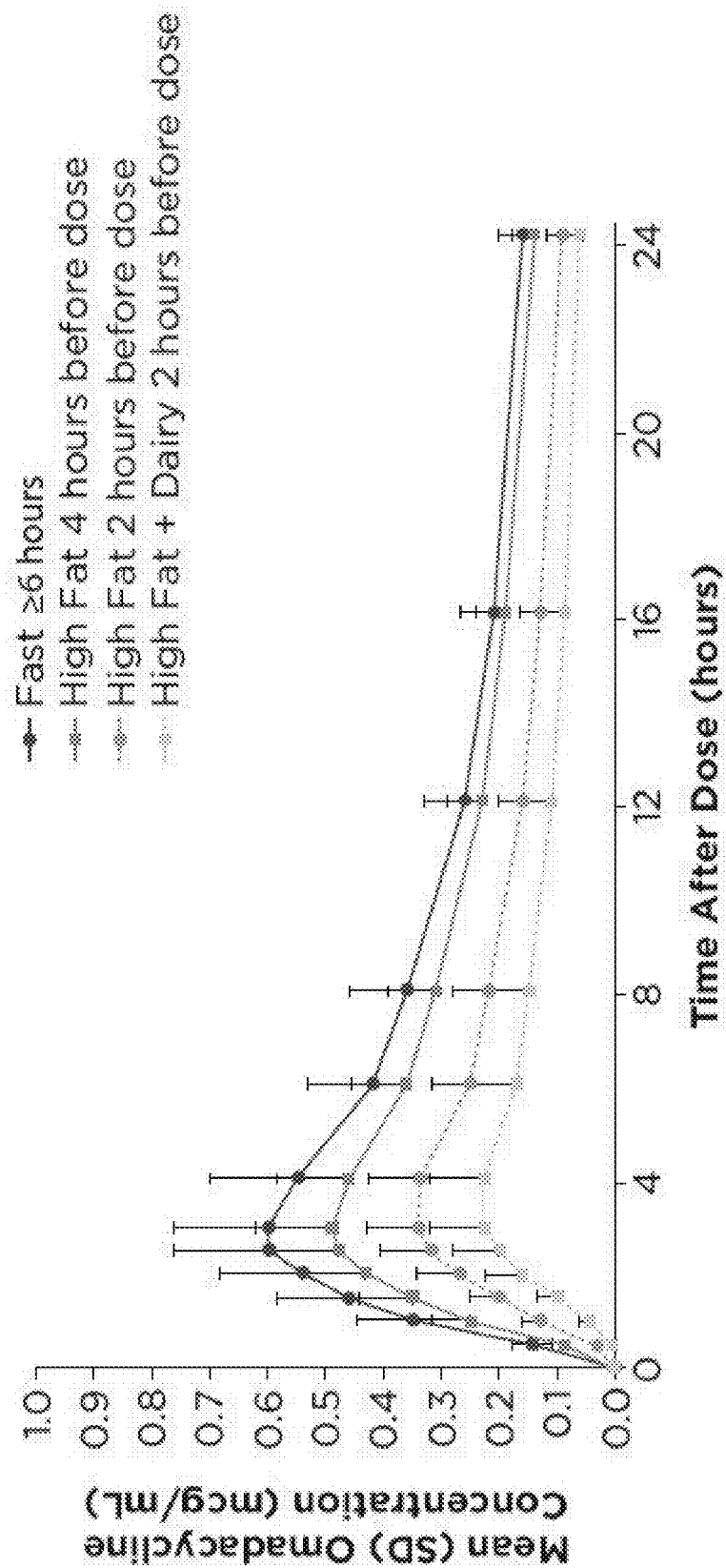
FIG. 1 shows plasma concentration-time curve for a single oral 300 mg dose of omadacycline.

Omadacycline (9-[(2,2-dimethyl-propyl amino)-methyl]-minocycline) is very active in vitro against most Gram-positive pathogens. For example, it has been shown to be effective in treating complicated Skin and Skin Structure Infections (see U.S. Pat. No. 9,265,740, incorporated herein by reference). It also exhibits activity against atypical pathogens (e.g., *Legionella* spp.), and some anaerobic and Gram-negative pathogens. The drug is active against strains expressing both mechanisms of tetracycline resistance as well as strains that are resistant to currently available antibiotics, including methicillin, vancomycin, erythromycin, and ciprofloxacin. Omadacycline also has demonstrated activity against the most common ABSSSI pathogens, including isolates resistant to standards of care.

Omadacycline has been developed for both i.v. and p.o. (oral) administration. To date, over 1000 subjects have received one or both formulations in completed clinical studies.

In completed Phase 1 studies, single i.v. doses up to 600 mg and single p.o. doses up to 600 mg have been investigated. Multiple i.v. doses of 100 mg once daily and 200 mg once daily for up to 14 and 7 consecutive days, respectively, have been investigated. Multiple p.o. doses of 200 mg once daily and 300 mg once daily for up to 10 consecutive days have been investigated. In addition, multiple p.o. doses of 450 mg once daily and 600 mg once daily for 5 consecutive days have also been investigated.

In a Phase 2 study, 219 subjects with complicated skin and skin structure infections (cSSSI) were treated with omadacycline (n=111) or linezolid (n=108); treatment was initiated with i.v. administration (100 mg per day), with switch to p.o. therapy (200 mg per day) at the discretion of the investigator. In this study the total duration of study treatment was a mean of 10 and maximum of 20 days.

In a sponsor terminated Phase 3 study of similar design, 140 subjects with cSSSI were treated with omadacycline (n=68) or linezolid (n=72) for a mean of 10 and maximum of 20 days for omadacycline and 22 days for linezolid. Patients were initially treated with study drug omadacycline IV (100 mg per day), and then switched to oral therapy at the discretion of the Investigator (300 mg per day). The expected duration of IV treatment was 4-7 days; the expected total duration of treatment (IV and oral) was up to 14 days. The study was double-blinded during the IV treatment phase and Evaluator-blinded during the oral treatment phase.

In a recently completed Phase 3 study comparing omadacycline and linezolid for the treatment of adults with ABSSSI, subjects started therapy with omadacycline 100 mg i.v. every 12 hours (q12h) for 2 doses then 100 mg i.v. every 24 hours (q24h), or linezolid 600 mg i.v. q12h. Subjects could be switched to oral therapy (omadacycline 300 mg q24h or linezolid 600 mg q12h) after a minimum of 3 days of i.v. therapy; the total treatment duration was 7-14 days. Study results showed that omadacycline was non-inferior to linezolid. In the FDA primary analysis population (defined as ITT subjects without a sole Gram-negative pathogen(s) at screening, total N=627) for omadacycline versus linezolid, respectively, clinical success based on a reduction of lesion size at 48-72 hours after the first dose was 84.8% versus 85.5% (95% confidence interval [CI]: −6.3, 4.9); clinical success based on investigator's assessment of clinical response at 7-14 days after the last dose was 86.1% versus 83.6% (CI: −3.2, 8.2). Omadacycline was well tolerated: treatment-emergent adverse events (TEAEs) were reported in 48.3% versus 45.7%; serious TEAEs in 3.4% versus 2.5% and discontinuation due to TEAE in 1.9% versus 2.2% of omadacycline and linezolid treated subjects, respectively.

In all the above studies, however, a portion of the dosing regimen requires i.v. administration of omadacycline, thus necessitating hospital visit and/or stay, or time spent in an outpatient infusion center. In an effort to develop an effective oral only dosing regimen that eliminates hospital visits, thus particularly desirable for treating community-acquired bacterial skin or skin structure infections (e.g., ABSSSI or cSSSI), an initial oral only dosing regimen was developed, in which a human subject in need of treatment for a bacterial skin or skin structure infection is given omadacycline orally, at a dose comparable to that used in the recently completed Phase 3 study: i.e., about 300 mg BID (twice daily, 300 mg each time, administered about 12 hours apart) for one day, followed by a dose of about 300 mg per day for a total of 7-14 days. Of note, a prior Phase 1 study has demonstrated that a 300 mg oral dose using the tablet formulation of omadacycline is bioequivalent (based on serum AUC) to a 100 mg i.v. dose.

Omadacycline was found to have a significant food effect, in that food consumption has a significant impact on the oral bioavailability of orally administered 300 mg dose of omadacycline. See Example 1. A PK study in healthy volunteers showed that, compared with a fasted dose, bioavailability was reduced by 15% to 17% for a nondairy meal 4 hours before dosing, 40% to 42% for a nondairy meal 2 hours before dosing, and 59% to 63% for a dairy meal 2 hours before dosing. Thus, the effect of food was more pronounced when a high-fat meal was consumed closer to dosing and when dairy was included in the meal. Based on this result, oral omadacycline should be administered at least 6 hours following a meal in order to achieve maximum bioavailability for the oral dose designed to achieve therapeutic efficacy.

This food effect poses a significant patient compliance challenge, particularly when two oral doses are to be administered in one day at the beginning of the dosing regimen.

Preliminary results of a Phase 1 study showed that oral dosing regimens of 300 mg QD (q24h) and 450 mg QD (q24h) had similar and favorable tolerability profiles. In addition, PK results and PK modeling indicate that a regimen of 450 mg p.o. QD (q24h) for 2 doses followed by 300 mg p.o. QD (q24h) achieves approximately the same steady state concentrations within the same time frame as a dosing regimen starting with 300 mg p.o. q12h for 2 doses, then 300 mg p.o. QD (q24h). In both regimens, a total of 900 mg oral omadacycline is administered over the first 2 days. See Example 2.

Thus in one aspect, the invention provides a method of treating a human subject in need of treatment for a bacterial skin or skin structure infection.

In a 1$^{st}$ embodiment, the method comprises orally administering to the subject an effective amount of 9-[(2,2-dimethyl-propyl amino)-methyl]-minocycline or a salt thereof, such that the subject is treated, wherein the 9-[(2,2-dimethyl-propyl amino)-methyl]-minocycline is administered as once-daily oral dose of 450 mg or 600 mg for 5 or more days.

In a 2$^{nd}$ embodiment, the method comprises orally administering to the subject an effective amount of 9-[(2,2-dimethyl-propyl amino)-methyl]-minocycline or a salt thereof, such that the subject is treated, wherein the 9-[(2,2-dimethyl-propyl amino)-methyl]-minocycline is administered as once-daily oral dose of 300 mg, for 5, 6, 7, or 8 consecutive days.

In a 3$^{rd}$ embodiment, the once-daily oral dose of the 1$^{st}$ embodiment is 450 mg, administered for 5 or more consecutive days.

In a 4$^{th}$ embodiment, the once-daily oral dose of the 1$^{st}$ embodiment is 600 mg, administered for 5 or more consecutive days.

In a 5$^{th}$ embodiment, the method comprises orally administering to the subject an effective amount of 9-[(2,2-dimethyl-propyl amino)-methyl]-minocycline or a salt thereof, such that the subject is treated, wherein the 9-[(2,2-dimethyl-propyl amino)-methyl]-minocycline is administered with an oral loading dose (e.g., a dose higher than once-daily oral dose of 300 mg), followed by once-daily oral doses of 300-600 mg (e.g., 300 mg, 450 mg, or 600 mg) for 5 or more days.

In a 6$^{th}$ embodiment, the oral loading dose of the 5$^{th}$ embodiment consists essentially of/consists of one oral dose of 600 mg of the 9-[(2,2-dimethyl-propyl amino)-methyl]-minocycline, administered 24 hours before the first of the once-daily oral doses of 300, 450, or 600 mg.

In a 7$^{th}$ embodiment, the oral loading dose of the 5$^{th}$ embodiment essentially of/consists of one oral dose of 450 mg of the 9-[(2,2-dimethyl-propyl amino)-methyl]-minocycline, administered 24 hours before the first of the once-daily oral doses of 300, 450, or 600 mg.

In an 8$^{th}$ embodiment, the oral loading dose of the 5$^{th}$ embodiment consists essentially of/consists of two oral doses of 300 mg of the 9-[(2,2-dimethyl-propyl amino)-methyl]-minocycline, administered 12 hours and 24 hours, respectively, before the first of the once-daily oral doses of 300 mg, 450 mg, or 600 mg.

In a 9$^{th}$ embodiment, the oral loading dose of the 5$^{th}$ embodiment consists essentially of/consists of two oral doses of 450 mg of the 9-[(2,2-dimethyl-propyl amino)-methyl]-minocycline, administered 12 hours and 24 hours, respectively, before the first of the once-daily oral doses of 300 mg, 450 mg, or 600 mg.

In a 10$^{th}$ embodiment, the oral loading dose of the 5$^{th}$ embodiment consists essentially of/consists of two oral dose of 600 mg of the 9-[(2,2-dimethyl-propyl amino)-methyl]-minocycline, administered 24 hours and 48 hours, respectively, before the first of the once-daily oral doses of 300 mg, 450 mg, or 600 mg.

In a 11$^{th}$ embodiment, the oral loading dose of the 5$^{th}$ embodiment consists essentially of/consists of two oral dose of 450 mg of the 9-[(2,2-dimethyl-propyl amino)-methyl]-minocycline, administered 24 hours and 48 hours, respectively, before the first of the once-daily oral doses of 300 mg, 450 mg, or 600 mg.

In a 12$^{th}$ embodiment, the method comprises orally administering to the subject an effective amount of 9-[(2,2-dimethyl-propyl amino)-methyl]-minocycline (omadacycline) or a salt thereof, such that the subject is treated, wherein the 9-[(2,2-dimethyl-propyl amino)-methyl]-minocycline is administered orally, at a dose of about 450 mg per day for two consecutive days, then at a dose of about 300 mg per day for 5 or more days, e.g., for a total treatment duration of 7-14 days.

As used herein, "bacterial skin and skin structure infection" is an infection of skin and associated soft tissues, such as loose connective tissue and mucous membranes. The pathogen involved in the bacterial skin and skin structure infection is a bacterial species. Such infections often requires treatment by antibiotics, such as the subject 9-[(2,2-dimethyl-propyl amino)-methyl]-minocycline.

In a $13^{th}$ embodiment, the bacterial skin or skin structure infection of any one of the $1^{st}$-$12^{th}$ embodiments is wound infection, cellulitis/erysipelas, major abscess, furuncles/boils, carbuncle, Staphylococcal scalded skin syndrome (SSSS), or ecthyma.

In a $14^{th}$ embodiment, the bacterial skin or skin structure infection of any one of the $1^{st}$-$12^{th}$ embodiments is Acute Bacterial Skin and Skin Structure Infection (ABSSSI), which most commonly include wound infection, cellulitis/erysipelas, and major abscess.

ABSSSI accounts for nearly 10% of hospital admissions and 3.4-3.8 million emergency department visits per year in the United States. Analyses of hospital discharge records indicate that 74% of ABSSSI admissions involve empiric treatment with methicillin-resistant *Staphylococcus aureus* (MRSA) active antibiotics.

In a $15^{th}$ embodiment, the ABSSSI of the $14^{th}$ embodiment is community-acquired ABSSSI.

In a $16^{th}$ embodiment, the community-acquired ABSSSI of the $15^{th}$ embodiment is caused by community-associated MRSA infection.

In a $17^{th}$ embodiment, the ABSSSI of any one of the $14^{th}$-$16^{th}$ embodiment is greater than or equal to 75 cm$^2$ in total surface area of contiguous involved tissue.

In an $18^{th}$ embodiment, the ABSSSI of any one of the $14^{th}$-$17^{th}$ embodiment comprises wound infection, cellulitis/erysipelas, and/or major abscess.

In a $19^{th}$ embodiment, the bacterial skin or skin structure infection (e.g., ABSSSI) of the $14^{th}$ embodiment is an infection prompting or occurring during hospitalization.

In a $20^{th}$ embodiment, the ABSSSI of any one of the $1^{st}$-$19^{th}$ embodiments is moderate to severe ABSSSI.

In a $21^{st}$ embodiment, the bacterial skin or skin structure infection of any one of the $1^{st}$-$20^{th}$ embodiments is a result of (or results from) skin injury, including but not limited to trauma, a surgical procedure, or IV drug use.

In a $22^{nd}$ embodiment, the bacterial skin or skin structure infection of any one of the $1^{st}$-$20^{th}$ embodiments is a result of (or results from) vascular insufficiency or edema.

In a $23^{rd}$ embodiment, the human subject of any one of the $1^{st}$-$22^{nd}$ embodiments is administered 9-[(2,2-dimethyl-propyl amino)-methyl]-minocycline orally under fasting condition.

For example, the human subject administered omadacycline has had no food, antacids, or multivitamins containing multivalent cations (e.g., aluminum, magnesium, calcium, bismuth, iron, or zinc), or drink, except water, for at least 6 hours before each dosing; and, after each dosing, will take no food for 2 hours, no dairy products, antacids, or multivitamins containing multivalent cations (e.g., aluminum, magnesium, calcium, bismuth, iron, or zinc) for 4 hours.

In a $24^{th}$ embodiment, the 9-[(2,2-dimethyl-propyl amino)-methyl]-minocycline of any one of the $1^{st}$-$23^{rd}$ embodiments is administered once per day (e.g., each oral dose is administered about 24 hours apart). For example, the human subject may take the oral dose of omadacycline in the morning, after fasting overnight for at least 6 hours.

In a $25^{th}$ embodiment, the subject of any one of the $1^{st}$-$24^{th}$ embodiments is treated up to and including about 14 days, up to and including about 13 days, up to and including about 12 days, up to and including about 11 days, up to and including about 10 days, up to and including about 9 days, up to and including about 8 days, or up to and including about 7 days, up to and including about 6 days, up to and including about 5 days, or up to and including about 4 days, such that the subject is treated.

In a $26^{th}$ embodiment, the subject of the $25^{th}$ embodiment is treated for 7-10 days.

In a $27^{th}$ embodiment, the subject of the $25^{th}$ embodiment is treated for 8 days.

In a $28^{th}$ embodiment, the salt of any one of the $1^{st}$-$27^{th}$ embodiments is a tosylate salt of 9-[(2,2-dimethyl-propyl amino)-methyl]-minocycline/omadacycline.

In a $29^{th}$ embodiment, the bacterial skin or skin structure infection of any one of the $1^{st}$-$28^{th}$ embodiments is known or suspected to be caused by Gram-positive pathogens.

In a $30^{th}$ embodiment, the Gram-positive pathogens of the $29^{th}$ embodiments may include (without limitation) *Staphylococcus aureus, Staphylococcus lugdunensis, Streptococcus* species, *Streptococcus agalactiae, Streptococcus mitis, Enterococcus* species (*Enterococcus faecalis* (such as VRE or VSE), or *Enterococcus faecium* (such as VRE or VSE)), *Streptococcus anginosus* group (*S. anginosus, S. constellatus,* and *S. intermedius,* that is beta-, alpha- or non-hemolytic), *Viridans* group Streptococci (VGS), *Clostridium perfringens, Finegoldia magna,* or a combination thereof.

In a $31^{st}$ embodiment, the *Staphylococcus aureus* of the $30^{th}$ embodiment is methicillin-resistant *Staphylococcus aureus* (MRSA), or methicillin-susceptible *Staphylococcus aureus* (MSSA).

In a $32^{nd}$ embodiment, the *Streptococcus* species of the $30^{th}$ embodiment include *Streptococcus anginosus* group.

In a $33^{rd}$ embodiment, the *Streptococcus* species of the $30^{th}$ embodiment include beta-hemolytic Streptococci or *S. anginosus.*

In a $34^{th}$ embodiment, the *Streptococcus* species of the $30^{th}$ embodiment include non-hemolytic Streptococci or *S. intermedius.*

In a $35^{th}$ embodiment, the *Streptococcus* species of the $30^{th}$ embodiment include alpha-hemolytic Streptococci or *S. constellatus.*

In a $36^{th}$ embodiment, the *Enterococcus* species of the $30^{th}$ embodiment include *Enterococcus faecalis* (VSE).

In a $37^{th}$ embodiment, the *Streptococcus* species of the $30^{th}$ embodiment include *Streptococcus pyogenes.*

In a $38^{th}$ embodiment, the bacterial skin or skin structure infection of any one of the $1^{st}$-$28^{th}$ embodiments is known or suspected to be caused by Gram-negative pathogens.

In a $39^{th}$ embodiment, the Gram-negative pathogens of the $38^{th}$ embodiment include *Enterobacter cloacae, Escherichia coli, Klebsiella pneumoniae, Prevotella denticola, Prevotella melaninogenica,* or a combination thereof.

In a $40^{th}$ embodiment, GI adverse events (AEs) associated with treatment (if any), in any one of the $1^{st}$-$39^{th}$ embodiments, are predominantly mild.

In a $41^{st}$ embodiment, GI adverse events (AEs) associated with treatment (if any), in any one of the $1^{st}$-$40^{th}$ embodiments, do not result in discontinuation of therapy.

In a $42^{nd}$ embodiment, the method of any one of the $1^{st}$-$41^{st}$ embodiments, has a greater clinical success rate than linezolid (N-[[3-(3-fluoro-4-morpholinophenyl)-2-oxooxazolidin-5-yl]methyl]acetamide), where the linezolid is administered at 600 mg orally every 12 hours.

In a 43rd embodiment, in any one of the 1st-42nd embodiments, successful Early Clinical Response (ECR) (e.g., 48 to 72 hours after the first dose), defined as survival with a greater than or equal to 20% reduction of lesion size compared to pre-treatment measurement (without receiving any rescue antibacterial therapy), is achieved in the human subject.

In a 44th embodiment, in any one of the 1st-43rd embodiments, successful Clinical Response (CR) is achieved in the human subject after treatment completion, wherein successful Clinical Response is defined as survival with resolution or improvement of one or more signs and symptoms of infection to the extent that further antibacterial therapy is not necessary.

In a 45th embodiment, in any one of the 1st-44th embodiments, $AUC_{0-24}$ after the first two doses of 9-[(2,2-dimethyl-propyl amino)-methyl]-minocycline or a salt thereof is about 9,000 ng*h/mL, 9,500 ng*h/mL, 10,000 ng*h/mL, or 10,500 ng*h/mL, or between any of the two above numbers.

In a 46th embodiment, in any one of the 1st-45th embodiments, each dose of the 9-[(2,2-dimethyl-propyl amino)-methyl]-minocycline or salt thereof is administered as 150 mg tablets. That is, 3 tablets for 450 mg oral dose, 2 tablets for 300 mg oral dose.

In a 47th embodiment, the method of any one of the 1st-46th embodiments has a clinical success rate of about 70-100%.

In a 48th embodiment, the clinical success rate of the 47th embodiment is about 80-100%, about 79-98%, about 79-94%, about 84-98%, about 80-88%, or about 84-89%.

In a 49th embodiment, the clinical success rate of the 47th or the 48th embodiment is observed at 48-72 hours after the first oral dose, and is about 79-94%, or about 84-89%, or about 87.5%.

In a 50th embodiment, the ABSSSI of the 49th embodiment consists essentially of wound infection, and the clinical success rate is about 84-94%, or about 89%.

In a 51st embodiment, the ABSSSI of the 49th embodiment consists essentially of cellulitis/erysipelas, and the clinical success rate is about 74-84%, or about 79%.

In a 52nd embodiment, the ABSSSI of the 49th embodiment consists essentially of major abscess, and the clinical success rate is about 90-98%, or about 94%.

In a 53rd embodiment, the clinical success rate of the 47th or the 48th embodiment is overall clinical success rate observed at about 7-14 days after the last dose of treatment, and is about 79-98%, about 75-95%, about 79-89%, 84%, about 95-100%, or about 98%.

In a 54th embodiment, the ABSSSI of the 53rd embodiment consists essentially of wound infection, and the overall clinical success rate is about 80-85%, or is about 82-83%.

In a 55th embodiment, the ABSSSI of the 53rd embodiment consists essentially of cellulitis/erysipelas, and the overall clinical success rate is about 85-91%, about 87-88%, or is about 88%.

In a 56th embodiment, the ABSSSI of the 53rd embodiment consists essentially of major abscess, and the overall clinical success rate is about 80-88%, or about 84%.

In a 57th embodiment, in any one of the 1st-56th embodiments, the 9-[(2,2-dimethyl-propyl amino)-methyl]-minocycline or salt thereof has an efficacy greater than linezolid for the treatment of the bacterial skin or skin structure infection (e.g., ABSSSI). Linezolid is N-[[3-(3-fluoro-4-morpholinophenyl)-2-oxooxazolidin-5-yl]methyl]acetamide, marked under the trademark ZYVOX™. In certain embodiments, linezolid is administered at 600 mg orally or 600 mg intravenously every 12 hrs.

In a 58th embodiment, in any one of the 1st-57th embodiments, the 9-[(2,2-dimethyl-propyl amino)-methyl]-minocycline or salt thereof is administered with a pharmaceutically acceptable carrier.

In a 59th embodiment, the pharmaceutically acceptable carrier of the 58th embodiment is acceptable for oral administration.

In a 60th embodiment, in any one of the 1st-59th embodiments, the method has a clinical success rate, e.g., that based on a reduction of lesion size at 48-72 hours after the first dose of about 80%, 81%, 82%, 83%, 84%, 85%, 86%, 87%, 88%, 89%, 90% or greater.

In a 61st embodiment, in any one of the 1st-60th embodiments, the method has a clinical success rate, e.g., clinical success based on investigator's assessment of clinical response at 7-14 days (e.g., 7-10 days, or 7, 8, 9, 10 days) after the last dose of about 80%, 81%, 82%, 83%, 84%, 85%, 86%, 87%, 88%, 89%, 90%, 91%, 92%, 93%, 94%, 95%, 96%, 97%, 98%, 99% or greater.

In a 62nd embodiment, in any one of the 1st-61st embodiments, the human subject has concurrent bacteremia.

In a 63rd embodiment, in any one of the 1st-62nd embodiments, the human subject is obese (e.g., those with BMI≥30).

In a 64th embodiment, in any one of the 1st-63rd embodiments, the human subject has mild-to-moderate renal impairment.

In a 65th embodiment, in any one of the 1st-64th embodiments, the human subject has hepatic impairment.

In a 66th embodiment, in any one of the 1st-65th embodiments, the human subject is over 45 yrs old, over 50 yrs old, over 55 yrs old, over 60 yrs old, over 65 yrs old, over 70 yrs old, or over 75 yrs old.

In a 67th embodiment, in any one of the 1st-66th embodiments, the human subject is an IV drug user.

Further details of the various embodiments are described below.

2. Definitions

"ABSSSI" or "Acute Bacterial Skin and Skin Structure Infection," is also sometimes referred to skin and soft tissue infection (SSTI). It is a type of infection of skin and associated soft tissues, such as loose connective tissue and mucous membranes. The FDA of the U.S. Department of Health and Human Services published in October 2013 a document entitled "Guidance for Industry Acute Bacterial Skin and Skin Structure Infections: Developing Drugs for Treatment" ("the Guidance," incorporated herein by reference), to assist sponsors in the clinical development of drugs for the treatment of ABSSSI. The Guidance defines ABSSSI as cellulitis/erysipelas, wound infection, and major cutaneous abscess with a measured surface area of greater than or equal to 75 cm². The Guidance does not address less serious skin infections, such as impetigo, and minor cutaneous abscess, as well as infections needing more complex treatment regimens, such as infections resulting from animal or human bites, necrotizing fasciitis, diabetic foot infection, decubitus ulcer infection, myonecrosis, and ecthyma gangrenosum or infections less than 75 cm² that may require antibiotic treatment.

Thus in certain embodiments, ABSSSI as used herein includes cellulitis/erysipelas, wound infection, and major cutaneous abscess. In certain embodiments, the cellulitis/erysipelas, wound infection, and/or major cutaneous abscess has a minimum lesion surface area of approximately 75 cm$^2$. The lesion size can be measured by the area of redness, edema, or induration.

In certain embodiments, for areas of ABSSSI that involve certain body surface sites, such as the face, or for young children appropriate and eligible for a phase 3 clinical trial, ABSSSI may include lesions with a surface area smaller than 75 cm$^2$, such as about 70 cm$^2$, 65 cm$^2$, 60 cm$^2$, 55 cm$^2$, 50 cm$^2$, 45 cm$^2$, or about 40 cm$^2$.

In certain embodiments, ABSSSI may involve certain body locations, such as on the face, near the eye, or on the hand, where lesions may be smaller than even 40 cm$^2$ but may still be treated with antibiotic.

In certain other embodiments, ABSSSI does not include lesions with a surface area smaller than 75 cm$^2$.

The size of the treatable skin and skin structure infection can be measured by the total surface area of contiguous involved tissue. Methods to assess lesion size generally include, but are not limited to, the following: (1) manual measurement of length multiplied by perpendicular width; (2) digital planimetry; and (3) computer-assisted tracings. For example, the total surface area of contiguous involved tissue can be calculated as the product of the maximum length (head-to-toe) multiplied by the maximum width (measured perpendicular to length) as measured by using, e.g., a wound ruler.

In certain embodiments, ABSSSI as used herein includes cellulitis/erysipelas, wound infection, major cutaneous abscess, as well as less serious skin infections, such as impetigo, and minor cutaneous abscess (e.g., those with lesion surface area of less than 75 cm$^2$). In other embodiment, ABSSSI does not include less serious skin infections, such as impetigo, and minor cutaneous abscess.

"Involved tissue" is defined as tissue exhibiting evidence of one or more of the following: erythema, edema or induration.

"Wound infection" includes an infection characterized by purulent drainage from a wound with surrounding erythema, edema, and/or induration. In certain embodiments, the surrounding erythema, edema, and/or induration extends at least 5 cm in the shortest distance from the peripheral margin of the wound.

"Cellulitis/erysipelas" includes a diffuse skin infection characterized by spreading areas of erythema, edema, and/or induration.

"Major abscess" includes an infection characterized by a collection of pus within the dermis or deeper with surrounding erythema, edema, and/or induration. In certain embodiments, the surrounding erythema, edema, and/or induration extends at least 5 cm in the shortest distance from the peripheral margin of the abscess.

Common bacterial pathogens causing ABSSSI include but are not limited to: *Streptococcus pyogenes* and *Staphylococcus aureus* including methicillin-resistant *S. aureus*, as well as the less common causes include other *Streptococcus* species, *Enterococcus faecalis*, or Gram-negative bacteria.

In certain embodiments, the ABSSSI is community acquired ABSSSI, which (as opposed to hospital-acquired ABSSSI) is contracted by a person with no or little contact with the healthcare system. In contrast, hospital-acquired ABSSSI is contracted by one who lives in long-term care facilities or have recently visited a hospital or other healthcare facility.

"Adverse Event (AE)" includes any untoward, undesired, or unplanned event in the form of signs, symptoms, disease, or laboratory or physiological observations occurring in a person given a dose or a series of doses of the subject 9-aminomethyl minocycline compound (9-[(2,2-dimethylpropyl amino)-methyl]-minocycline) during treatment.

The term "effective amount" here includes the amount of omadacycline needed to treat a bacterial infection. For example, an effective amount describes an efficacious level sufficient to achieve the desired therapeutic effect through the killing of bacteria and/or inhibition of bacterial growth. Preferably, the bacterial infection is treated when the pathogen (e.g., bacteria) is eradicated.

"Fasting condition," as used herein, includes giving the subject to be treated no food, antacids, or multivitamins containing multivalent cations (e.g., aluminum, magnesium, calcium, bismuth, iron, or zinc), or drink, except water, for at least 6 hours before each dosing; and, after each dosing, no food for 2 hours, no dairy products, antacids, or multivitamins containing multivalent cations (e.g., aluminum, magnesium, calcium, bismuth, iron, or zinc) for 4 hours.

"Furuncles/boils" includes deep bacterial infection of hair follicles.

"Carbuncle" includes coalescence of multiple furuncles.

"Staphylococcal scalded skin syndrome (SSSS)" includes red blistering skin caused by exotoxins from toxigenic strains of the bacteria *Staphylococcus aureus*.

"Ecthyma" includes crusted erosions or ulcerations (a deep form of impetigo) caused by *Streptococcus pyogenes* and/or *Staphylococcus aureus*.

"Clinical Response" for ABSSSI can be based on the percent reduction in the lesion size at 48 to 72 hours compared to baseline, measured in patients who did not receive rescue therapy and are alive. A clinical response in a patient in this timeframe generally is defined as a percent reduction in lesion size greater than or equal to 20 percent compared to baseline.

Evidence of a systemic inflammatory response may be indicated by at least one of the following: elevated white blood cell (WBC) count (e.g., greater than or equal to 10,000 cells/mm$^3$) or leukopenia (e.g., less than or equal to 4,000 cells/mm$^3$); elevated immature neutrophils (e.g., greater than or equal to 15% band forms) regardless of total peripheral white blood cell (WBC) count; lymphatic involvement, e.g., lymphangitis or lymphadenopathy that is proximal to and in a location that suggests drainage from the qualifying infection; fever or hypothermia documented by a temperature of greater than about 38.0° C. [100.4° F.] or less than 36.0° C. [95.5° F.].

The term "treating" or "treatment" refers to the amelioration, eradication, or diminishment of one or more symptoms of the disorder, e.g., a bacterial skin or skin structure infection (e.g., ABSSSI), to be treated. In certain embodiments, the disorder term includes the eradication of bacteria associated with the infection to be treated.

The term "prophylaxis" means to prevent or reduce the risk of bacterial infection.

The term "resistance" or "resistant" refers to the antibiotic/organism standards as defined by the Clinical and Laboratories Standards Institute (CLSI) and/or the Food and Drug Administration (FDA).

"Pharmaceutically acceptable carrier" includes substances capable of being co-administered with the 9-[(2,2-dimethyl-propyl amino)-methyl]-minocycline or salt thereof, and which allow the drug compound to perform its intended function, e.g., treat or prevent a bacterial skin or skin structure infection. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

In certain embodiments, the pharmaceutically acceptable (inert) carriers are in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective omadacycline of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols.

When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

In certain embodiments, the 9-[(2,2-dimethyl-propyl amino)-methyl]-minocycline or salt thereof is formulated as a tablet with excipients including lactose monohydrate, microcrystalline cellulose, sodium stearyl fumarate, crospovidone, colloidal silicone dioxide, sodium bisulfite, polyvinyl alcohol, titanium dioxide, talc, glycerol monocaprylocaprate, sodium lauryl sulfate, and/or iron oxide yellow.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats. Also, omadacycline and salts thereof may be used to treat non-animal subjects, such as plants.

With the invention generally described above, the examples below further illustrates (but not limit) the invention described herein.

EXAMPLES

Example 1 Effect of Food on the Bioavailability of Omadacycline in Healthy Volunteers Omadacycline (OMC, 9-[(2,2-dimethyl-propyl amino)-methyl]-minocycline) is a first-in-class aminomethylcycline antibiotic that is characterized by improved in vitro antimicrobial activity (Honeyman et al, *Antimicrob Agents Chemother.* 59:7044-7053, 2015). It demonstrates in vitro activity against a broad range of Gram-positive and Gram-negative aerobes, many anaerobes, and atypical pathogens including *Legionella* spp. and *Mycoplasma* spp. (Macone et al, *Antimicrob Agents Chemother.* 58:1127-1135, 2014; Dubois et al, In vitro activity of omadacycline against *Legionella pneumophila*. Abstract presented at the 55th ICAAC, San Diego, Calif., Sep. 17-21, 2015; Kim et al, *Activity and efficacy of omadacycline against Clostridium difficile*. Abstract presented at the 2016 ECCMID, Amsterdam, the Netherlands). In patients with complicated skin and skin structure infection, omadacycline demonstrated clinical efficacy and tolerability that was comparable to linezolid (Noel. et al, *Antimicrob Agents Chemother.* 56:5650-5654, 2012; Noel et al, Safety and efficacy of PTK 0796 (omadacycline) as treatment of complicated skin and soft tissue infection (cSSTI). Poster presented at 23rd European Congress on Clinical Microbiology and Infectious Diseases, Mar. 31-Apr. 3, 2012, London, UK).

Phase 3 studies have concluded with omadacycline as oral and intravenous (IV) monotherapy in patients with acute bacterial skin and skin structure infection (ABSSSI).

During the development process, oral omadacycline formulations have evolved from free-base in a capsule through a series of tablet and salt formulations in order to optimize oral bioavailability while improving tolerability. The current phase 3 tablet formulation is the tosylate salt of omadacycline, which has been shown to have an absolute bioavailability of 34.5% when administered under fasting conditions. The primary objective of this study was to evaluate the relative bioavailability of a single oral 300 mg dose of omadacycline (administered as the phase 3 tablet formulation) at various times after the consumption of food in healthy adult subjects.

The result of this study showed that food consumption has an effect on the oral bioavailability of a single 300 mg OMC dose.

Briefly, the study was a phase 1, randomized, open-label 4-period, crossover study. Before dosing on Day 1 of Period 1, subjects were randomized to one of four treatment sequences (see Table 1). On Day 1 of each period, subjects received a single oral dose of 300 mg omadacycline (2×150 mg tablets) at various times after the consumption of food. There was a washout period of at least 5 days between each dosing period. A final study completion visit occurred 6 to 10 days after the last dose of omadacycline.

TABLE 1

Treatment Sequences

| Sequence | Period 1 | Period 2 | Period 3 | Period 4 |
|---|---|---|---|---|
| ADBC | A | D | B | C |
| BACD | B | A | C | D |
| CBDA | C | B | D | A |
| DCAB | D | C | A | B |

A: subjects fasted overnight (no food or drink except for water for at least 6 hours before dosing); a standard high-fat (nondairy) meal was served 3 hours after dosing
B: a standard high-fat (nondairy) meal completed at 4 hours before dosing
C: a standard high-fat (nondairy) meal completed at 2 hours before dosing
D: a standard high-fat meal including dairy completed at 2 hours before dosing The high-fat (approximately 50% of total caloric content of the meal) and high-calorie (approximately 800 to 1000 calories) meal followed Food and Drug Administration guidance recommendations, and provided approximately 150, 250, and 500 to 600 calories from protein, carbohydrate, and fat, respectively (FDA Guidance, 2002). These meals were to be consumed within 20 minutes. Dose administration for Treatments B, C, and D was based off of the end time of the meal. During all 4 treatment periods, subjects received no food or drink except water for at least 3 hours after dosing and no dairy products, antacids or multivitamins for 4 hours after dosing.

A total of 32 subjects were enrolled and dosed in at least one treatment period. Overall mean age was 32.3 years, with a range of 21 to 50 years; 47% were male (Table 2). One subject was discontinued from the study because of a positive alcohol screen at baseline of period 3 and did not receive Treatments A and D. One subject requested withdrawal and did not receive Treatments B and C. PK data were available for 31 subjects for each treatment condition.

TABLE 2

Baseline Demographics

|  | Subjects (n = 32) |
|---|---|
| Age, years[a] | 32.2 (8.0) |
| Age range, years | 21-50 |
| Male, n (%) | 15 (46.9) |
| Race, n (%) |  |
| white | 24 (75) |
| black/African American | 8 (25) |
| Hispanic/Latino | 12 (37.5) |
| Height, cm[a] | 168.0 (9.5) |
| Weight, kg[a] | 71.5 (13.4) |
| BMI (body Mass Index), kg/m$^{2a}$ | 25.2 (3.2) |

[a]Mean (Standard Deviation)

Blood samples for pharmacokinetic (PK) assessments of omadacycline were collected before dosing (predose) and at 0.5, 1, 1.5, 2, 2.5, 3, 4, 6, 8, 12, 16, and 24 hours after dosing in each period. PK parameters included: Area under the plasma concentration-time curve (AUC) from time 0 to 24 hours after dosing ($AUC_{0-24}$); AUC from time 0 to the last quantifiable concentration ($AUC_{0-t}$); AUC time 0 extrapolated to infinity ($AUC_{0-inf}$); Maximum (peak) observed plasma concentration ($C_{max}$); Time to reach $C_{max}$ ($T_{max}$); Terminal elimination half-life ($T_{1/2}$); Terminal phase rate constant ($\lambda z$).

Safety and tolerability was assessed by: Adverse events (AEs); vital sign measurements at multiple time-points within 24 hours post-dose in each treatment period; and clinical laboratory tests 24 hours post-dose in each treatment period.

For statistical analysis, individual PK parameters for omadacycline were summarized with descriptive statistics. Geometric means were determined for AUC and $C_{max}$. PK parameters were evaluated using non-compartmental analysis using Phoenix® WinNonlin® (Pharsight Corp, St. Louis, Mo.), Version 6.2.1. Confidence intervals (CI) for test treatments (fed states: Treatments B, C, and D) compared with the reference treatment (fasted state: Treatment A) were constructed for $AUC_{0-24}$, $AUC_{0-t}$, $AUC_{0-inf}$ and $C_{max}$. Absence of the effect of food was concluded if the 90% CI for the test-to-reference ratios (B/A, C/A, or D/A) of geometric means were contained within the criterion interval of 80% to 125% for $AUC_{0-24}$, $AUC_{0-t}$, $AUC_{0-inf}$ and $C_{max}$. For $T_{max}$, the Wilcoxon signed rank test was performed. $p \leq 0.05$ was considered statistically significant.

A linear mixed-effect model with treatment condition, sequence, and period as fixed effects and subject nested within sequence as a random effect was fitted to the natural log-transformed PK parameters for estimation of effects and 90% confidence intervals (CIs) for the fed states compared with the fasted state.

TABLE 3

Plasma PK Parameters for Omadacycline after a Single 300 mg Oral Dose

| | Mean (Coefficient of Variation) | | | |
|---|---|---|---|---|
| Parameter | Treatment A N = 31 | Treatment B N = 31 | Treatment C N = 31 | Treatment D N = 31 |
| $AUC_{0-24}$, mcg * h/mL | 7.2 (28.1) | 6.1 (26.3) | 4.2 (23.4) | 2.8 (44.3) |
| $AUC_{0-t}$, mcg * h/mL | 7.2 (28.1) | 6.1 (26.3) | 4.2 (23.4) | 2.8 (44.4) |
| $AUC_{0-inf}$, mcg * h/mL | 10.2 (27.0)[b] | 8.8 (29.2) | 6.0 (25.4) | 4.0 (44.1) |
| $C_{max}$, mcg/mL | 0.6 (25.3) | 0.6 (25.0) | 0.4 (22.4) | 0.3 (42.6) |
| $T_{max}$, h[a] | 2.5 (1.5, 4.1) | 2.9 (1.0, 6.0) | 2.9 (1.0, 6.0) | 2.9 (1.0, 6.0) |
| $T_{1/2}$, h | 13.8 (10.3)[b] | 13.6 (12.7) | 13.6 (12.2) | 13.5 (14.7) |

PK analysis showed that, for the 31 subjects included in the PK analysis, fasted $AUC_{0-inf}$, $AUC_{0-t}$, and $AUC_{0-24}$ were 10.2, 7.2, and 7.2 mcg*h/mL, respectively, and $C_{max}$ was 0.6 mcg/mL. Across all treatment periods, mean $T_{1/2}$ ranged from 13.5 to 13.8 hours, and median $T_{max}$ ranged from 2.5 to 2.9 hours. No treatment-related adverse events or clinically relevant changes in laboratory values, or vital signs occurred. See Table 3.

A significant reduction in systemic exposure to omadacycline was observed for all three treatments (Treatments B, C, and D) vs. Treatment A (FIG. 1 and Table 4).

TABLE 4

Statistical Analysis of the Effect of Food on Plasma
Pharmacokinetic Parameters of Omadacycline (N = 31)

| Parameter | Treatment | Geometric LS Mean | Treatment Comparison | Ratio of Geometric LS Mean (%) | 90% CI of Ratio (%) |
|---|---|---|---|---|---|
| $AUC_{0-24}$, mcg * h/mL | A | 7.4 | | | |
| | B | 6.2 | B/A | 83.4 | 74.9, 92.7 |
| | C | 4.3 | C/A | 57.7 | 51.9, 64.2 |
| | D | 2.8 | D/A | 37.3 | 33.6, 41.5 |
| $AUC_{0-t}$, mcg * h/mL | A | 7.4 | | | |
| | B | 6.2 | B/A | 83.3 | 74.9, 92.7 |
| | C | 4.3 | C/A | 57.7 | 51.9, 64.1 |
| | D | 2.8 | D/A | 37.3 | 33.5, 41.4 |
| $AUC_{0-inf}$, mcg * h/mL | A* | 10.6 | | | |
| | B | 9.0 | B/A | 84.7 | 75.8, 94.6 |
| | C | 6.2 | C/A | 58.4 | 52.3, 65.3 |
| | D | 4.0 | D/A | 37.9 | 34.0, 42.3 |
| $C_{max}$, mcg/mL | A | 0.66 | | | |
| | B | 0.56 | B/A | 84.5 | 75.9, 94.1 |
| | C | 0.39 | C/A | 60.1 | 54.0, 66.9 |
| | D | 0.27 | D/A | 40.7 | 36.5, 45.2 |

* N = 30, a terminal mono-exponential phase could not be identified for one subject.
CI, confidence interval;
LS, least squares The effect of food was more pronounced when a high-fat meal was consumed closer to dosing and when dairy was included in the meal. Compared with a fasted dose, omadacycline exposure ($C_{max}$ and AUC) was Reduced by 15% to 17% for a nondairy meal 4 hours before dosing; reduced by 40% to 42% for a nondairy meal 2 hours before dosing; and reduced by 59% to 63% for a dairy meal 2 hours before dosing. The between-subject variability in systemic exposure to omadacycline was similar for Treatments A, B and C (CV 22.4-29.2%) for $C_{max}$ and AUC. By contrast, for Treatment D the CV was 42.6-44.4% for these parameters.

Concerning safety and tolerability, two subjects experienced treatment emergent AEs (one reported nausea, one reported somnolence); both events were of mild intensity and considered unrelated to study drug. No subject discontinued the study for an AE, and no subject experienced a serious AE (SAE). A slight increase from baseline in heart rate (median 8 to 10 bpm at 4 to 6 hours post dose) was observed for Treatment A (i.e., the group with highest omadacycline exposure). In all other treatment groups, the median change from baseline in heart rate was ≤3 bpm at all measured time points. No notable changes in blood pressure were observed. There were no clinically significant changes in clinical laboratory tests.

The results showed that a single oral dose of omadacycline was well tolerated. Administration of a 300 mg dose within 2 to 4 hours of food reduced the bioavailability compared with the fasted state. Thus preferably, once daily oral omadacycline should be administered at least 6 hours following a meal.

Example 2 A Phase I, Randomized, Double-Blind, 3-Period, Crossover Study to Evaluate Safety, Tolerability, and Pharmacokinetics of Multiple Oral Doses of Omadacycline or Placebo in Healthy Adult Subjects The primary objective of this study was to assess and compare the pharmacokinetics (PK) of 300-, 450-, and 600-mg doses of oral omadacycline administered daily over 5 days. The secondary objective of the study was to evaluate the safety and tolerability of multiple doses of omadacycline in healthy adult subjects.

For the treatment of ABSSSI, the then anticipated therapeutic daily oral dose (excluding any loading dose) was 300 mg. For potential future studies, or for administration of a loading dose using the oral formulation, it is possible that a daily dose higher than 300 mg could be used to achieve omadacycline concentrations sufficient to treat target bacteria in the organs/tissues of interest. One early clinical study evaluated single oral doses of omadacycline up to 600 mg, but no studies have evaluated multiple daily doses higher than 300 mg. This study was designed to obtain data on the safety, tolerability, and pharmacokinetics (dose linearity and proportionality) of multiple oral doses of omadacycline at daily doses higher than 300 mg. Placebo groups were included as a reference to minimize potential bias in assessing tolerability.

Multiple daily oral doses of 300, 450, and 600 mg omadacycline or placebo were chosen to be administered in this study. The lowest dose of 300 mg had been evaluated in multiple dose studies and had been well tolerated; this daily dose has also been studied in Phase 3 studies in ABSSSI. Single oral doses up to 600 mg were administered in capsules to healthy adult subjects in 1 early clinical study and were determined to have an acceptable safety profile. There was some increased incidence of GI AEs at oral doses of 400 mg or greater, though events were typically mild (none were severe), and it is possible that some of these events may have been related to the oral formulation. Multiple daily doses of up to 600 mg using the final optimized tablet formulation of omadacycline were expected to have acceptable safety profiles, but this was important to assess in a small carefully controlled Phase 1 study before evaluating these doses in larger clinical studies.

Thus the study was designed as a Phase 1, randomized, double-blind, 3-period, crossover study in healthy adult subjects. The study consisted of a screening period (Day −21 through Day −2), 3 baseline periods (Day −1 of each period), 3 treatment periods (Day 1 through Day 6 of each period), and a study completion visit (within 6 to 10 days after the last dose of study drug in Period 3). There was a washout of at least 5 days between the last dose in one period and the first dose in the next period. Subjects were confined to the study site from Day −1 of Period 1 until discharge on Day 6 of Period 3, after the 24-hour blood sampling, urine sampling, and safety assessments were completed. Subjects returned to the study center 6 to 10 days after the last dose of study drug in Period 3 for the study completion visit.

Subject Selection

Healthy, non-smoking, male and female subjects were eligible for participation in the study if they were between 18 and 55 years of age (inclusive), weighed ≥50 kg, had a body mass index between 18 and 30 kg/m2 (inclusive), met all eligibility criteria during screening (performed within 21 days before dosing in Period 1) and at baseline (Day −1) for Period 1, and provided written informed consent. Health status was determined by past medical history, clinical laboratory tests, vital signs (oral body temperature, systolic blood pressure, diastolic blood pressure, and heart rate), 12-lead electrocardiogram (ECG), and physical examination at screening. Eligibility criteria included ability to swallow up to 4 tablets in succession.

Subjects were excluded from participation in the study for prior treatment with omadacycline, recent use of other investigational drugs; ECG abnormalities; inability to tolerate oral medications; pregnancy or breastfeeding; use of tobacco products, prescription drugs, herbal supplements, or over-the-counter medications or intake of xanthine (e.g., caffeine)—containing food or beverages within a specified time frame before study initiation; blood loss/donation; low hemoglobin levels; high creatinine or blood urea nitrogen levels; urinary obstruction/difficulty voiding; positive alcohol or drug test; hypersensitivity or allergy to any tetracycline; signs of liver disease or liver injury; significant illness within 2 weeks of study initiation; any planned medical intervention that might interfere with the study; or a history of diseases or medical conditions as specified in the study protocol.

Study Design

On Day 1 through Day 5 of each period, subjects received once-daily, after a fast of 6 hours, one of the following treatments (omadacycline or placebo) according to the randomization schedule:

A. 300 mg omadacycline (2×150-mg tablets)
AP. Placebo for 300 mg omadacycline (2×placebo tablets)
B. 450 mg omadacycline (3×150-mg tablets)
BP. Placebo for 450 mg omadacycline (3×placebo tablets)
C. 600 mg omadacycline (4×150-mg tablets)
CP. Placebo for 600 mg omadacycline (4×placebo tablets)

All doses of study drug were administered in the morning with no food or drink except for water at least 6 hours prior to dosing. Subjects then had no food or drink except water for at least 2 hours after dosing and no dairy products, antacids, or multivitamins for 4 hours after dosing.

Before the dosing, subjects underwent screening evaluations to determine eligibility within 21 days before dosing in Period 1. Subjects were then admitted to the clinical site on the day before dosing (Day −1 of Period 1) for baseline evaluations. Before dosing on Day 1 of Period 1, up to 30 subjects (24 omadacycline, 6 placebo) were randomly assigned to 1 of 3 treatment sequences using a Latin Square design as presented in the following table:

| Sequence | Subsequence | Number of Subjects | Period 1 | Period 2 | Period 3 |
|---|---|---|---|---|---|
| 1 | 1A | 8 omadacycline | A | C | B |
|  | 1B | 2 placebo | AP | CP | BP |
| 2 | 2A | 8 omadacycline | B | A | C |
|  | 2B | 2 placebo | BP | AP | CP |
| 3 | 3A | 8 omadacycline | C | B | A |
|  | 3B | 2 placebo | CP | BP | AP |

About ten subjects were randomly assigned to each sequence. Placebo was administered to 2 subjects in each sequence as a reference to assess tolerability. Subjects assigned to omadacycline received omadacycline during all 3 periods and at all tested dose levels. Subjects assigned to placebo received placebo during all 3 periods. Investigators and subjects were blinded to whether the subject was receiving omadacycline or placebo.

Study Assessment

1. Plasma Pharmacokinetics

Serial blood samples for pharmacokinetic (PK) analysis of omadacycline were collected at specified time points through 24 hours after dosing on Day 1 and Day 5 of each period. Specifically, blood samples for PK assessments of omadacycline were collected from all subjects at the following time points: before dosing (predose) and at 0.5, 1, 1.5, 2, 2.5, 3, 4, 6, 8, 12, 16, and 24 hours after dosing on Day 1 and Day 5 in each period. The 24-hour blood sample for Day 1 was collected prior to dosing on Day 2 for each period.

Non-compartmental PK parameters were determined on Days 1 and 5 of each period from plasma omadacycline concentration and actual time data using Phoenix® WinNonlin® (Certara, Princeton, N.J.) Version 6.2.1., including area under the plasma concentration versus time curve (AUC) from time 0 to 24 hours after dosing ($AUC_{0-24}$), AUC from time 0 to the last quantifiable concentration ($AUC_{last}$), maximum observed plasma concentration ($C_{max}$), time to reach maximum observed plasma concentration ($T_{max}$), terminal elimination half-life ($T_{1/2}$), terminal phase rate constant ($\lambda_z$) and the accumulation factor (Rac) of $AUC_{0-24}$ and $C_{max}$.

Subjects that received omadacycline and had at least one evaluable PK parameter were included in the PK analysis population; however, subjects may have been excluded from the PK population if they missed doses, had diarrhea, or had vomiting at or before a time equal to twice the median $T_{max}$.

2. Urine Pharmacokinetics

Urine samples were collected from a subset of subjects at specified intervals on Day 5 of Period 2 and on Day 1 and Day 5 of Period: predose, 0 to 4, 4 to 8, 8 to 12, and 12 to 24 hours after dosing. The 12 to 24-hour interval urine sample for Day 1 was collected prior to dosing on Day 2. Urine samples were only collected from a subset of subjects because analysis of urine PK was added by an amendment to the study protocol after the study was already underway.

The following urine PK parameters were determined from urine omadacycline concentration and collection interval data using SAS Version 9.2: renal clearance (CLr), fraction of the dose excreted unchanged in urine from 0 to 24 hours after dosing ($Fe_{0-24}$), and amount of drug excreted unchanged in urine over 24 hours after dosing ($Ae_{t1-t2}$). Additional parameters $Ae_{0-4}$, $Ae_{4-8}$, $Ae_{8-12}$, $Ae_{12-24}$, and $Ae_{0-24}$ were also calculated.

3. Safety and Tolerability

Safety assessments include monitoring of adverse events (AEs), clinical laboratory test results, vital sign measurements, 12-lead electrocardiogram (ECG) results, and physical examination findings. All randomly assigned subjects who received at least one dose of any study drug (omadacycline or placebo) were included in the safety analysis population. Adverse events were coded by preferred term and system organ class using MedDRA Version 17.1.

Safety and tolerability were assessed by the monitoring and recording of AEs, clinical laboratory test results (hematology, serum chemistry, and urinalysis), vital sign measurements (oral body temperature, systolic blood pressure, diastolic blood pressure, and HR), 12-lead ECG results, and physical examination findings.

Statistical Analysis for Pharmacokinetic Study:

Individual plasma and urine concentration and time deviation data were presented in data listings. Plasma and urine concentration data were summarized by day and time point or interval for each treatment using descriptive statistics (number of subjects, mean, SD, coefficient of variation [CV], median, minimum, and maximum). Concentrations that were below the limit of quantification (BLQ) were treated as zero in the plasma and urine concentration descriptive statistics summaries. Mean and individual plasma concentration versus time profiles were presented in figures on both linear and semilogarithmic scales.

Non-compartmental PK parameters were determined from plasma concentration and actual time data using Phoenix® WinNonlin® (Certara, Princeton, N.J.) Version 6.2.1 or higher. Urine PK parameters were determined from urine concentration and collection interval data using SAS Version 9.2 or higher. All further statistical analyses were performed using SAS® software (SAS Institute, Cary, N.C.), Version 9.2.

For the PK analysis, BLQ values were treated as zero with the exception that a BLQ value between 2 quantifiable concentrations were set as missing. Missing concentrations were treated as missing from the PK parameter calculations. If consecutive BLQ concentrations were followed by quantifiable concentrations in the terminal phase, those concentrations after BLQ concentrations were treated as missing.

The individual PK parameters were presented in data listings. Descriptive statistics (number of subjects, mean, SD, CV, median, minimum, and maximum) were calculated for the PK parameter estimates after dosing on Day 1 and Day 5 of each period (e.g., $AUC_{0-24}$, $AUC_{last}$, $C_{max}$, $T_{max}$, $T_{1/2}$, and Rac [Day 5 only] from plasma concentrations; CLr, $Fe_{0-24}$, and $Ae_{0-24}$ from urine concentrations). Geometric means were included for $AUC_{0-24}$, $AUC_{last}$, and $C_{max}$.

A linear mixed-effect model (SAS PROC MIXED) with treatment (A, B, and C), sequence (1A, 2A, and 3A), and treatment period as fixed effects and subject nested within sequence as a random effect were fitted to the natural log-transformed dose normalized PK parameters $AUC_{0-24}$/Dose, $AUC_{last}$/Dose, and $C_{max}$/Dose after dosing on Day 1 and Day 5 of each period for use in estimation of effects and construction of confidence intervals (CIs). Point estimates and 90% CIs for differences on the log scale were exponentiated to obtain estimates for the ratios of geometric means and respective 90% CIs on the original scale. No adjustment was made for multiplicity.

Dose linearity across all 3 dose levels was assessed by fitting omadacycline $C_{max}$, $AUC_{last}$, and $AUC_{0-24}$ after both the Day 1 and Day 5 doses to a power model (10): $\ln(PK) = a + b \times \ln(Dose) + error$, where PK was the PK parameter, a was the intercept and b was the slope. The estimates of slope b were reported along with the corresponding 2-sided 90% CIs.

For statistical analysis of accumulation of omadacycline, a linear mixed-effect model with day as a fixed effect and subject as random effect was fitted to the natural log-transformed $C_{max}$ and $AUC_{0-24}$ to construct 90% CIs for Day 5 compared with Day 1 (at each dose level separately).

Results a. Demographics, Baseline Characteristics, and Disposition of Study Subjects Of the 33 subjects enrolled in the study, 26 were assigned to receive omadacycline and 7 were assigned to receive placebo. Demographic and baseline characteristics were generally similar between omadacycline and placebo treatment groups (Table 2-1) and across all omadacycline treatment sequences (data not shown). The majority of subjects in the study were white (57.6%) and male (81.8%). The overall mean age of subjects was 36.9 years, with a range of 21 to 55 years.

TABLE 2-1

Demographics and Baseline Characteristics of Subjects in the Study[a]

| | Omadacycline (N = 26) | Placebo (N = 7) | Overall (N = 33) |
|---|---|---|---|
| Age, years | | | |
| Mean (±SD) | 35.6 (±10.4) | 41.9 (±11.6) | 36.9 (±10.8) |
| Min, max | 21, 55 | 25, 53 | 21, 55 |
| Sex, n (%) | | | |
| Male | 21 (80.8) | 6 (85.7) | 27 (81.8) |
| Female | 5 (19.2) | 1 (14.3) | 6 (18.2) |
| Race, n (%) | | | |
| White | 15 (57.7) | 4 (57.1) | 19 (57.6) |
| Black or African American | 9 (34.6) | 3 (42.9) | 12 (36.4) |
| Asian | 2 (7.7) | 0 | 2 (6.1) |
| Ethnicity, n (%) | | | |
| Hispanic or Latino | 10 (38.5) | 3 (42.9) | 13 (39.4) |
| Not Hispanic or Latino | 16 (61.5) | 4 (57.1) | 20 (60.6) |

TABLE 2-1-continued

Demographics and Baseline Characteristics of Subjects in the Study[a]

|  | Omadacycline (N = 26) | Placebo (N = 7) | Overall (N = 33) |
|---|---|---|---|
| Height, cm | | | |
| Mean (±SD) | 173.12 (±9.17) | 172.89 (±4.31) | 173.07 (±8.32) |
| Min, max | 155.2, 192.4 | 165.6, 177.4 | 155.2, 192.4 |
| Weight, kg | | | |
| Mean (±SD) | 78.67 (±10.33) | 83.77 (±4.80) | 79.75 (±9.60) |
| Min, max | 62.7, 101.4 | 76.7, 90.4 | 62.7, 101.4 |
| Body mass index, kg/m² | | | |
| Mean (±SD) | 26.25 (±2.72) | 28.04 (±1.45) | 26.63 (±2.59) |
| Min, max | 19.4, 29.8 | 25.8, 29.9 | 19.4, 29.9 |

[a]Results for Safety Population

All 33 subjects received at least one dose of study drug (omadacycline or placebo) and were included in the safety analysis population. Twenty-five of the 26 omadacycline-treated subjects (96.2%) were included in the PK analysis population (one subject was excluded from this population due to vomiting after dosing). Four omadacycline-treated subjects (15.4%) and one placebo-treated subject (14.3%) discontinued the study; these early discontinuations were due to treatment-emergent adverse events (TEAEs) in 4 subjects (see below); in addition one omadacycline-treated subject was lost to follow-up. Thus, 22 subjects received all 5 doses of 300-, 450-, and 600-mg omadacycline and 6 subjects received all 5 doses of placebo in Periods 1, 2, and 3. These subjects were considered to have completed the study.

b. Plasma Pharmacokinetics

The preliminary results of the PK study at the end of Day 1 and Day 5 were summarized below.

| Doses | Day 1 PK Summary | |
|---|---|---|
| 300 | Mean | 6,560.73 |
|  | SD | 1,688.07 |
|  | CV % | 25.7% |
|  | Geom. Mean | 6,293.65 |
|  | Lower 90% CI | 3,630.22 |
|  | Upper 90% CI | 10,911.21 |
| 450 | Mean | 8,959.13 |
|  | SD | 2,397.56 |
|  | CV % | 27% |
|  | Geom. Mean | 8,382.03 |
|  | Lower 90% CI | 3,795.01 |
|  | Upper 90% CI | 18,513.38 |
| 600 | Mean | 9,990.20 |
|  | SD | 2,577.37 |
|  | CV % | 26% |
|  | Geom. Mean | 9,644.67 |
|  | Lower 90% CI | 5,962.46 |
|  | Upper 90% CI | 15,600.89 |

| Doses | Day 5 PK Summary | |
|---|---|---|
| 300 | Mean | 9,351.02 |
|  | SD | 2,461.74 |
|  | CV % | 26.3% |
|  | Geom. Mean | 8,990.55 |
|  | Lower 90% CI | 5,358.92 |
|  | Upper 90% CI | 15,083.28 |
| 450 | Mean | 13,363.54 |
|  | SD | 3,469.26 |
|  | CV % | 26.0% |
|  | Geom. Mean | 12,883.95 |
|  | Lower 90% CI | 7,849.02 |
|  | Upper 90% CI | 21,148.66 |
| 600 | Mean | 16,171.61 |
|  | SD | 4,501.33 |
|  | CV % | 27.8% |
|  | Geom. Mean | 15,431.37 |
|  | Lower 90% CI | 8,683.23 |
|  | Upper 90% CI | 27,423.79 |

Figure 2:
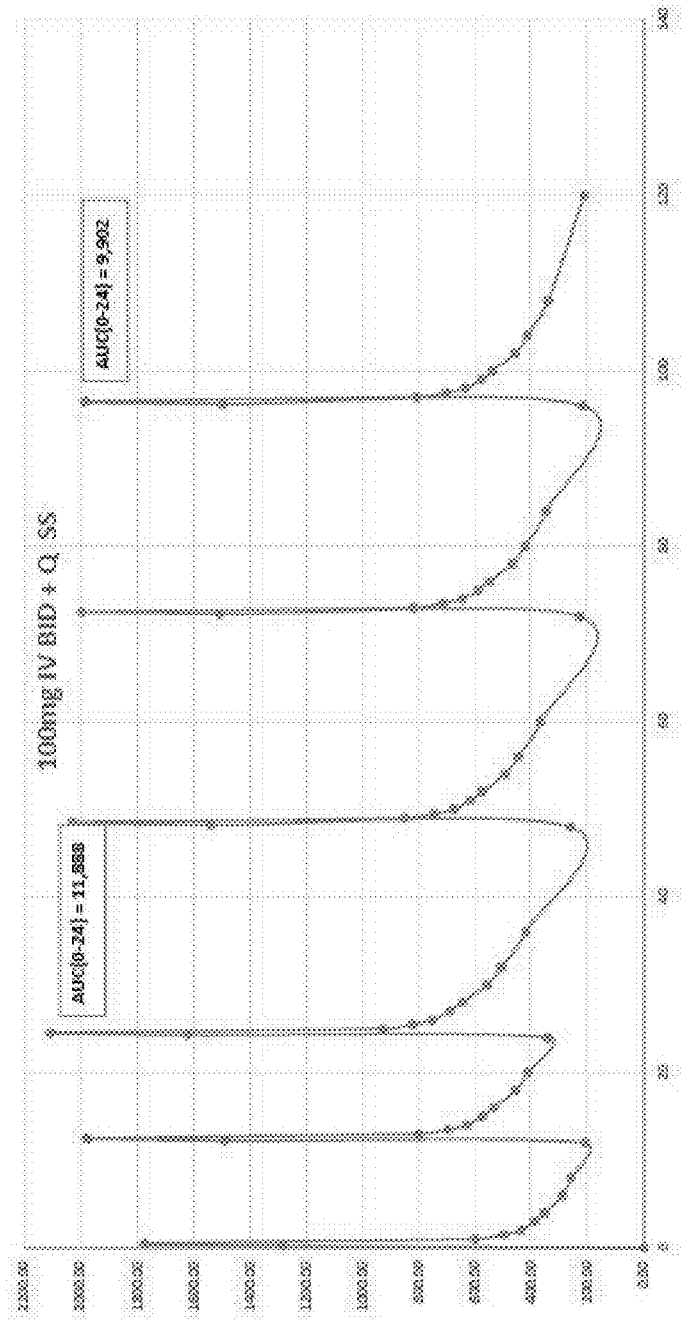
FIG. 2 shows PK data for a dosing regimen, in which 100 mg of omadacycline is administered i.v. BID (twice a day, administered 12 hrs apart) for 1 day, followed by 100 mg i.v. per day.
Figure 3:
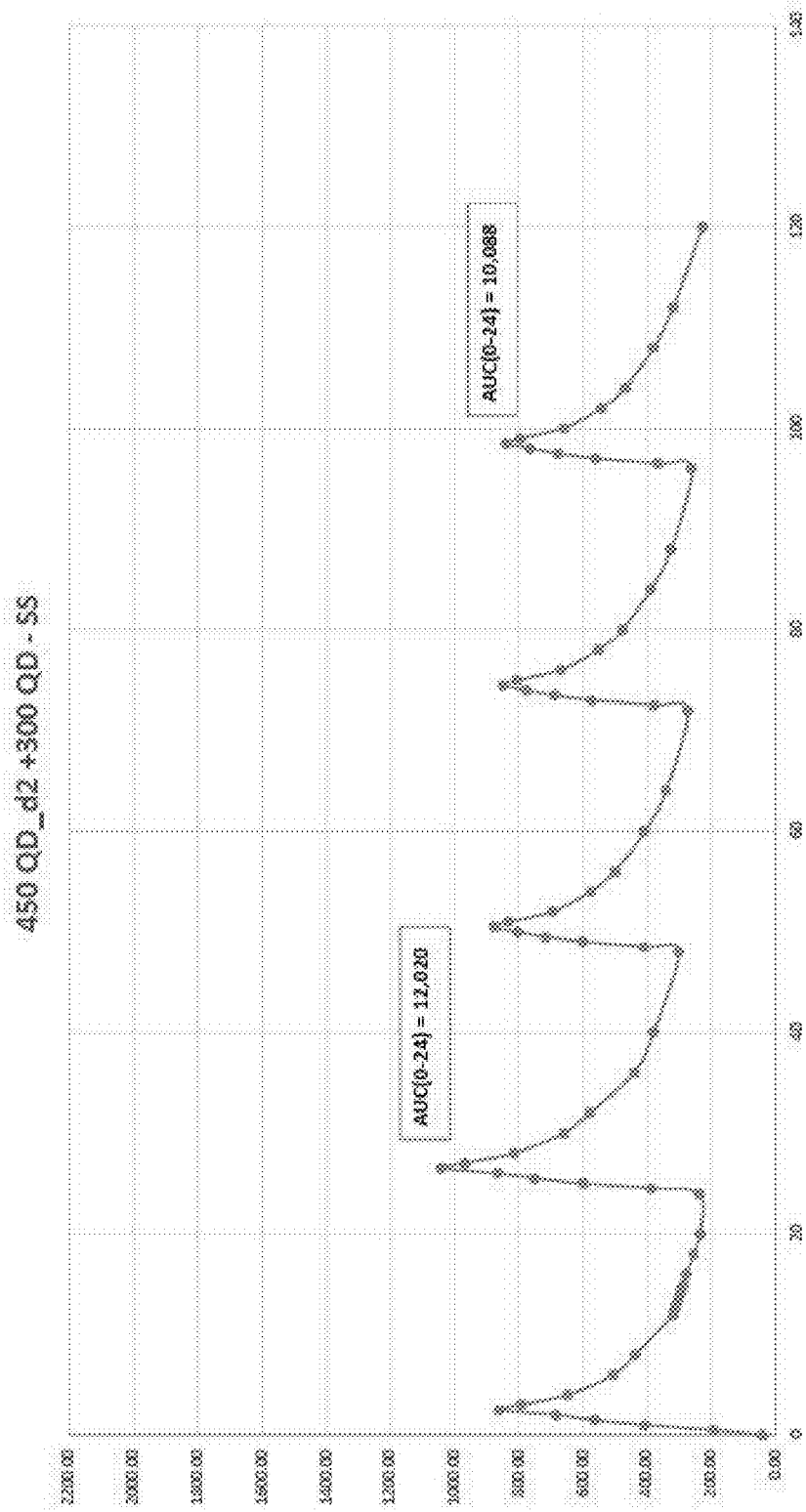
FIG. 3 shows PK data for a dosing regimen, in which 450 mg of omadacycline is administered p.o. QD (once a day) for 2 days, followed by 300 mg p.o. per day.
Figure 4:
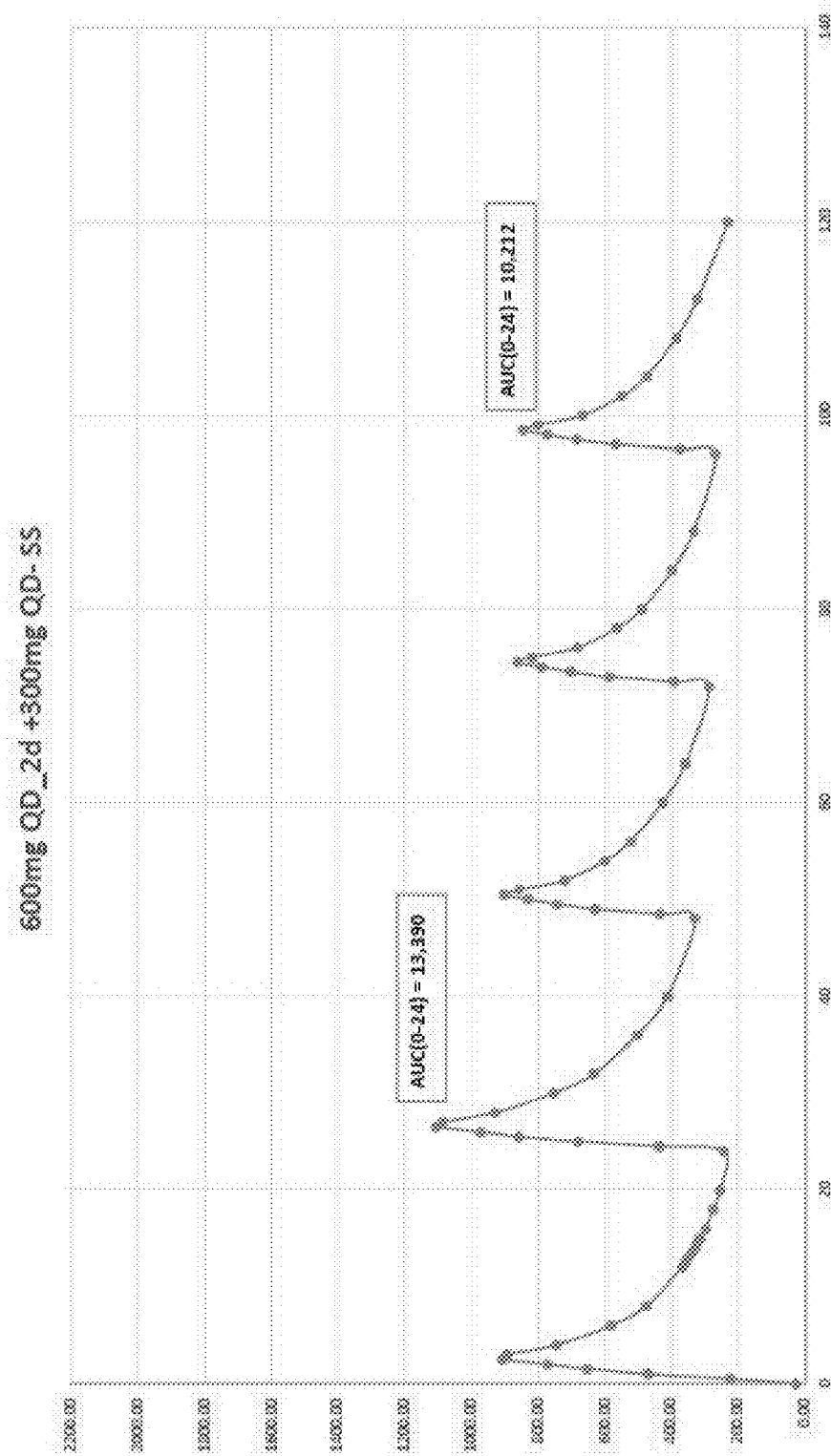
FIG. 4 shows PK data for a dosing regimen, in which 600 mg of omadacycline is administered p.o. QD (once a day) for 2 days, followed by 300 mg p.o. per day.

Using pharmacokinetic data from this and other Phase 1 studies, PK models for the following dosing regimens have been constructed, and the results were presented in FIGS. 2-4.

Specifically, FIG. 2 showed PK data for a dosing regimen, in which 100 mg of omadacycline was administered i.v. BID (twice a day, administered 12 hrs apart) for 1 day, followed by 100 mg i.v./day).

FIG. 3 showed PK data for a dosing regimen, in which 450 mg of omadacycline was administered p.o. QD (once a day) for 2 days, followed by 300 mg p.o./day.

FIG. 4 showed PK data for a dosing regimen, in which 600 mg of omadacycline was administered p.o. QD (once a day) for 2 days, followed by 300 mg p.o./day.

It is apparent that $AUC_{0-24}$ for the dosing regimens shown in FIGS. 2 and 3 were nearly identical.

More detailed data analysis were presented below.

Figure 5:
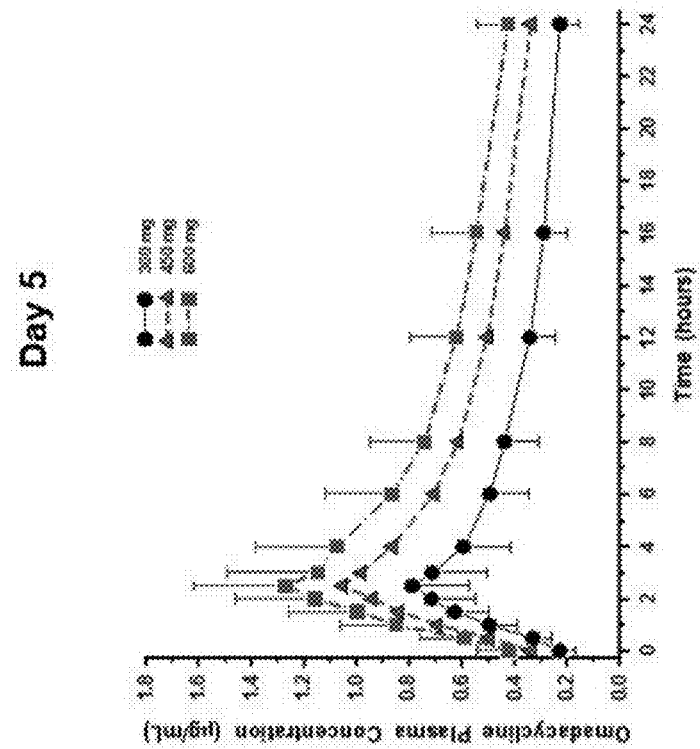
FIG. 5 shows plasma concentration versus time curves of omadacycline after oral administration. Mean (±SD) plasma concentrations of omadacycline versus time are shown by omadacycline dose (300, 450, or 600 mg) for the pharmacokinetic population. Oral omadacycline doses were administered at time 0 on each of 5 consecutive days of dosing in each of 3 periods. Blood samples were collected for PK analysis on Day 1 (left panel) and Day 5 (right panel). Data was pooled by omadacycline dose for all subjects regardless of the period in which they received a particular dose.
Figure 5:
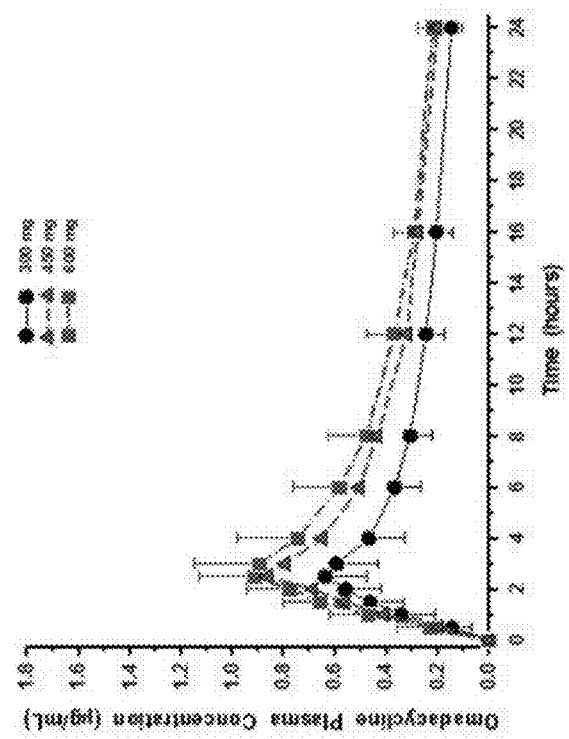

At all tested omadacycline dose levels on both Day 1 and Day 5 of each 5-day treatment period, mean plasma omadacycline concentrations peaked 2.5 hours after dosing ($T_{max}$) and omadacycline was measurable in plasma for up to 24 hours after dosing (the last sampling time) (FIG. 5 and Table 2-2).

TABLE 2-2

Plasma Pharmacokinetic Parameters of Omadacycline by Dose on Days 1 and 5 of Dosing[a]

| | Omadacycline Dose | | | | | |
|---|---|---|---|---|---|---|
| | Day 1 | | | Day 5 | | |
| Parameter | 300 mg (n = 25) | 450 mg (n = 24) | 600 mg (n = 24) | 300 mg (n = 23) | 450 mg (n = 24) | 600 mg (n = 23) |
| Mean $AUC_{0-24}$, ng · h/mL | 6644.8 | 8976.5 | 10020.5 | 9267.2 | 13366.7 | 16420.3 |
| (CV) | (25.3) | (26.6) | (25.7) | (26.8) | (26.0) | (27.1) |
| Mean $C_{max}$, ng/mL | 648.8 | 874.2 | 954.5 | 808.8 | 1077.3 | 1305.5 |
| (CV) | (24.0) | (26.6) | (23.2) | (25.9) | (25.0) | (26.6) |
| Mean $T_{max}$, h | 2.50 | 2.50 | 2.51 | 2.50 | 2.50 | 2.50 |
| (Min, max) | (1.50, 3.00) | (1.50, 3.00) | (1.00, 3.00) | (1.00, 3.00) | (1.50, 4.00) | (2.00, 4.00) |
| Mean $T_{1/2}$, h | 13.66 | 13.45 | 13.03 | 15.49 | 16.83 | 16.75 |
| (CV) | (12.5)[b] | (12.9)[c] | (11.8)[c] | (10.7)[d] | (8.1)[c] | (6.8)[d] |

[a]Results for Pharmacokinetic Population
[b]n = 24 ($T_{1/2}$ was not estimable for 1 subject)
[c]n = 23 ($T_{1/2}$ was not estimable for 1 subject)
[d]n = 21 ($T_{1/2}$ was not estimable for 2 subjects)
CV, coefficient of variation
Note:
One 300 mg omadacycline subject and one 600 mg omadacycline subject were excluded from the Day 5 summary due to vomiting before reaching the pharmacokinetic steady state on Day 5

Omadacycline total exposure ($AUC_{0-24}$ and $AUC_{last}$) and peak concentrations ($C_{max}$) increased with increasing omadacycline dose (300 vs 450 vs 600 mg) on both Day 1 and Day 5, and were higher on Day 5 than on Day 1 for corresponding doses (FIG. 5 and Table 2-2). The mean half-life of omadacycline in plasma ($T_{1/2}$) was similar across the 3 tested dose levels, ranging from 13.03 to 13.66 hours on Day 1 and from 15.49 to 16.83 hours on Day 5 (Table 2-2). Between-subject variability in systemic omadacycline exposure was low and was similar at all three tested dose levels, with coefficients of variation (CVs) ranging from 23.2% to 26.6% for $C_{max}$, $AUC_{0-24}$, and $AUC_{last}$ on Day 1 and from 25.0% to 27.1% for $C_{max}$, $AUC_{0-24}$, and $AUC_{last}$ on Day 5 (Table 2-2).

Although omadacycline $AUC_{0-24}$, $AUC_{last}$ and $C_{max}$ increased with increasing omadacycline dose, the observed increases in exposure were less than dose proportional on both days of analysis (Tables 2-2 and 2-3).

TABLE 2-3

Statistical Analysis of Dose-Normalized Omadacycline Pharmacokinetic Parameters on Days 1 and 5 of Dosing[a]

| Parameter | Treatment | N | Geometric LS Means | Treatment Comparison | Ratio of Geometric LS Means (%) | 90% CI of Ratio (%) |
|---|---|---|---|---|---|---|
| Day 1 | | | | | | |
| $AUC_{0-24}$/Dose | 300 mg | 25 | 21.32 | 450/300 | 87.44 | (77.41, 98.77) |
| (ng · h/mL/mg) | 450 mg | 24 | 18.64 | 600/450 | 86.79 | (76.71, 98.20) |
| | 600 mg | 24 | 16.18 | 600/300 | 75.89 | (67.20, 85.71) |
| $C_{max}$/Dose | 300 mg | 25 | 2.09 | 450/300 | 86.71 | (76.17, 98.71) |
| (ng/mL/mg) | 450 mg | 24 | 1.81 | 600/450 | 85.26 | (74.76, 97.23) |
| | 600 mg | 24 | 1.54 | 600/300 | 73.92 | (64.95, 84.14) |
| Day 5 | | | | | | |
| $AUC_{0-24}$/Dose | 300 mg | 23 | 30.09 | 450/300 | 95.82 | (90.39, 101.59) |
| (ng · h/mL/mg) | 450 mg | 24 | 28.83 | 600/450 | 91.78 | (86.58, 97.30) |
| | 600 mg | 23 | 26.46 | 600/300 | 87.95 | (82.96, 93.25) |
| $C_{max}$/Dose | 300 mg | 23 | 2.62 | 450/300 | 88.58 | (83.19, 94.32) |
| (ng/mL/mg) | 450 mg | 24 | 2.32 | 600/450 | 90.72 | (85.20, 96.60) |
| | 600 mg | 23 | 2.11 | 600/300 | 80.36 | (75.47, 85.58) |

[a]Results for Pharmacokinetic Population ANOVA analysis; see Materials and Methods for details
CI, confidence interval;
LS, least squares
Note:
One 300 mg omadacycline subject and one 600 mg omadacycline subject were excluded from the Day 5 statistical analysis due to vomiting before reaching the pharmacokinetic steady state on Day 5

Statistical analyses showed that with an increase in dose from 300 mg to 600 mg, omadacycline exposure (based on dose-normalized $AUC_{0-24}$) on Day 1 was 76% of that predicted if exposure were perfectly dose-proportional (Table 2-3); on Day 5, the observed increase in omadacycline exposure was 88% of predicted (Table 2-3). Analysis of $C_{max}$ values similarly demonstrated that omadacycline concentrations were dose-linear, but less than dose-proportional in this study (Tables 2-2 and 2-3).

Statistical analyses also revealed accumulation of omadacycline in plasma following once-daily dosing for 5 consecutive days. Depending on dose, accumulation ratios between Day 5 and Day 1 ranged from 1.40 to 1.62 for $AUC_{0-24}$ and from 1.24 to 1.35 for $C_{max}$ (data not shown). These findings are consistent with the long half-life of omadacycline in plasma.

The above data showed that mean concentrations of omadacycline peaked at 2.5 hours and remained measurable up to 24 hours (the last tested time point) at all omadacycline dosing levels (300, 450, and 600 mg). On Day 5, mean steady state exposure ($AUC_{0-24}$) in subjects dosed with 300-mg omadacycline was 9267 ng·h/mL, which is consistent with results of previous studies with 300 mg oral dosing. Both $AUC_{0-24}$ and $C_{max}$ increased with increasing dose and were nearly, but somewhat less than, dose-proportional (74%-88% of expected). This was the case on both Day 1 and Day 5 of dosing. Due to its relatively long half-life (mean=~13 h on Day 1, ~16 h on Day 5), omadacycline accumulated in plasma over the course of 5 consecutive days of dosing. Thus, at all tested dose levels, systemic exposure on Day 5 was ~50% higher than on Day 1. This degree of accumulation is also consistent with that observed following multiple once-daily dosing of IV or oral formulations of omadacycline in early pharmacology studies.

In terms of systemic exposure, this study showed that omadacycline plasma concentrations on Day 1 of 450-mg dosing were similar to those on Day 5 of 300-mg dosing (mean $AUC_{0-24}$=8976.5 and 9267.2 ng·h/mL, respectively). For indications in which the therapeutic dosing regimen incorporates 300 mg daily oral dosing, these data support a strategy of using an initial oral "loading dose" of 450 mg once-daily for 1-2 days, followed by 300-mg once-daily oral dosing. Such a strategy could potentially eliminate the need for an IV phase of treatment and is currently being evaluated in an ongoing phase 3 trial of oral-only omadacycline treatment in patients with ABSSSI (ClinicalTrials.gov ID, NCT02877927).

c. Urine Pharmacokinetics

Because urine sample collection and PK analysis were added to the study by protocol amendment after the study was underway, only a limited number of samples were evaluated (samples from 9 subjects on Day 5 of Period 2 and samples from 8 subjects on Day 1 and Day 5 of Period 3). While this sample size was too small to make meaningful comparisons between omadacycline dose groups, the results of the analysis did provide an overall indication of partial omadacycline renal clearance and urinary excretion.

For all omadacycline dose groups, the mean fraction of the dose excreted unchanged in urine from 0 to 24 hours after dosing ($Fe_{0-24}$) ranged from ~5% to ~7% on Day 1 and from ~7% to ~9% on Day 5. Renal clearance (CLr) ranged from 2.8 to 4.2 L/h on Day 1 and from 2.4 to 3.3 L/h on Day 5 (Table 2-4).

TABLE 2-4

Urine Pharmacokinetic Parameters of Omadacycline by Dose on Days 1 and 5 of Dosing[a]

| | Omadacycline Dose | | | | | |
|---|---|---|---|---|---|---|
| | Day 1 | | | Day 5 | | |
| Parameter[b] | 300 mg (n = 2) | 450 mg (n = 3) | 600 mg (n = 1) | 300 mg (n = 3) | 450 mg (n = 5) | 600 mg (n = 4) |
| $Ae_{0-24}$ (mg) | 20.37 (8.3) | 25.06 (16.8) | 31.96 | 26.14 (14.6) | 30.81 (33.0) | 51.82 (14.8) |
| $Fe_{0-24}$ (%) | 6.79 (8.3) | 5.57 (16.8) | 5.33 | 8.71 (14.6) | 6.85 (33.0) | 8.64 (14.8) |
| CLr (L/h) | 3.01 (11.4) | 2.80 (9.6) | 4.17 | 3.28 (27.2) | 2.38 (34.9) | 3.05 (19.9) |

[a]Results for Pharmacokinetic Population
[b]Mean (CV)
CV, coefficient of variation
Note:
One 600 mg omadacycline subject was excluded from the summary due to vomiting before reaching the pharmacokinetic steady state on Day 5

Urine PK analyses in a subset of subjects provided preliminary indications of partial renal clearance and urinary excretion of omadacycline. On Day 5, depending on dose level, ~7% to ~9% of the administered oral dose was excreted unchanged in the urine over 24 hours. This represents approximately 20% to 25% of the absorbed dose since it is known that the absolute bioavailability of the tablet formulation used in this study is 35%. Presence of unchanged omadacycline in the urine suggests that it may be useful in urinary tract infections, an indication that is currently being explored.

d. Safety and Tolerability

Overall, 12 of the 33 subjects in the safety population reported a total of 36 TEAEs during the study (Table 2-5).

TABLE 2-5

Summary of Treatment-Emergent Adverse Events[a]

| | Omadacycline Dose | | | Omadacycline | Placebo |
|---|---|---|---|---|---|
| | 300 mg (n = 26) | 450 mg (n = 24) | 600 mg (n = 24) | Overall (n = 26) | Overall (n = 7) |
| | n (%) of subjects with: | | | | |
| Any TEAE | 5 (19.2) | 3 (12.5) | 6 (25.0) | 10 (38.5) | 2 (28.6) |
| Treatment-related TEAE | 4 (15.4) | 2 (8.3) | 6 (25.0) | 9 (34.6) | 1 (14.3) |

TABLE 2-5-continued

Summary of Treatment-Emergent Adverse Events[a]

| | Omadacycline Dose | | | Omadacycline | Placebo |
|---|---|---|---|---|---|
| | 300 mg (n = 26) | 450 mg (n = 24) | 600 mg (n = 24) | Overall (n = 26) | Overall (n = 7) |
| Most frequent TEAEs (seen in >1 study subject), n (%) | | | | | |
| Nausea | 2 (7.7) | 1 (4.2) | 4 (16.7) | 6 (23.1) | 0 |
| Vomiting | 2 (7.7) | 0 | 1 (4.2) | 3 (11.5) | 0 |
| Diarrhea | 0 | 0 | 2 (8.3) | 2 (7.7) | 0 |
| Dizziness | 2 (7.7) | 0 | 1 (4.2) | 3 (11.5) | 0 |
| ALT increased | 0 | 1 (4.2) | 1 (4.2) | 2 (7.7) | 0 |
| TEAEs leading to early discontinuation of study drug, n (%) | | | | | |
| All | 1 (3.8) | 1 (4.2) | 1 (4.2) | 3 (11.5) | 1 (14.3) |
| Nausea | 1 (3.8) | 0 | 0 | 1 (3.8) | 0 |
| Vomiting | 1 (3.8) | 0 | 0 | 1 (3.8) | 0 |
| ALT increased | 0 | 1 (4.2) | 0 | 1 (3.8) | 0 |
| Lipase increased | 0 | 0 | 1 (4.2) | 1 (3.8) | 0 |
| Syncope | 0 | 0 | 0 | 0 | 1 (14.3)[b] |

[a]Results for Safety Population
[b]vasovagal syncope following a blood draw
ALT, alanine aminotransferase; TEAE, treatment-emergent adverse event TEAEs were reported by 38.5% of subjects that received omadacycline and 28.6% of subjects that received placebo. The highest percentage of TEAEs was classified as gastrointestinal (GI) disorders. The most frequently reported TEAE was nausea, which occurred in ≤7.7% of the omadacycline 300 and 450 mg dose groups and 16.7% of the 600 mg group. All of the TEAEs reported in this study were either mild or moderate in severity. There were no serious TEAEs (SAEs) reported during the study. Four subjects experienced TEAEs leading to study discontinuation, including one subject at each of the 3 omadacycline dose levels and 1 subject in the placebo group.

There were no clinically significant findings in analyses of vital sign measurements, physical examination, ECG results, hematology or urinalysis parameters. Serum chemistry analyses showed that between baseline and Day 5 of each dosing period, the median change in alanine aminotransferase (ALT) concentration was −2.0, 5.0 and 19.5 IU/L in subjects dosed with 300, 450 and 600 mg omadacycline, respectively. The corresponding changes in placebo groups ranged from −5.0 to −1.0 IU/L. No substantial changes in median aspartate aminotransferase (AST), bilirubin or other serum chemistry parameters were noted. The highest individual ALT value was 150 IU/L (2.7-fold above the upper limit of normal [ULN]), which occurred in a subject who first received 450 mg omadacycline in Period 1 then 300 mg in Period 2 and then was discontinued due to the liver enzyme changes; this subject's bilirubin values remained within the normal range at all time points assessed.

The plasma PK findings indicate that higher systemic drug exposure can be achieved by increasing the amount of omadacycline administered per dose during once-daily oral dosing, but that the exposure benefit is not dose-proportional. Moreover, increasing omadacycline dosing beyond a certain point appears to have adverse effects in terms of safety and tolerability. While multiple doses of 300, 450, and 600 mg were all generally well-tolerated in this study (all TEAEs were either mild or moderate in severity), there were some differences between the doses. The frequency of treatment-related TEAEs did not increase with an increase in omadacycline dose from 300 to 450 mg (15.4% vs 8.3%), but such events were more frequent with 600 mg (25.0%).

Within the most frequent class of TEAEs, GI disorders, nausea occurred with incidence at least 9% higher for the 600 mg dose level than for the lower doses, and the only 2 reports of diarrhea occurred with 600 mg. In addition, serum chemistry analyses showed a small but notable dose-dependent increase in median ALT concentrations. While no individual ALT values exceeded 3-fold above the ULN, the higher median ALT at 600 mg suggests an increased chance of more significantly elevated serum transaminase levels with this dose. Based on these findings, for situations in which an oral dose above 300 mg may be beneficial, 450 mg was identified as the oral dose most likely to provide higher omadacycline exposure with favorable safety and tolerability.

In summary, this phase 1 study investigated the pharmacokinetics (PK) and safety/tolerability of multiple oral omadacycline doses higher than 300 mg. Using a 3-period crossover design, healthy adults were randomized to receive omadacycline (300-, 450- and 600-mg in variable sequence; n=26) or placebo (n=7) once daily for 5 consecutive days per period. In plasma, omadacycline maximum concentration and total exposure increased with increasing dose, but were less than dose-proportional (74% to 88% of expected). The kinetics of omadacycline plasma accumulation were similar between dose levels; exposure on Day 5 was ~50% higher than on Day 1. Omadacycline plasma concentrations on Day 1 of 450 mg dosing were similar to those on Day 5 of 300 mg dosing. Urine PK analyses indicated partial renal clearance and urinary excretion of unchanged omadacycline. All doses were generally well-tolerated. These results support the use of once-daily 450-mg oral omadacycline as part of the oral only dosing regimen, such as using once-daily 450-mg oral omadacycline (either one or two doses) as loading dose before stepping down to once-daily 300-mg oral omadacycline, or in a dosing regimen using once-daily 450-mg oral omadacycline throughout the treatment.

Example 3 A Phase 3 Randomized, Double-Blind, Multi-Center Study to Compare the Safety and Efficacy of Oral Omadacycline to Oral Linezolid for Treating Adult Subjects with Acute Bacterial Skin and Skin Structure Infection (ABSSSI)

9-[(2,2-dimethyl-propyl amino)-methyl]-minocycline, otherwise known as omadacycline (OMC), the first aminomethylcycline antibiotic, is a semi-synthetic derivative of the tetracycline class. As a class, the tetracyclines have been in use for approximately 70 years. They are well-tolerated, and have proven effective in the treatment of a variety of bacterial infections.

Omadacycline has demonstrated activity against the most common ABSSSI pathogens, including methicillin-resistant *Staphylococcus aureus* (MRSA). Omadacycline was evaluated in a Phase 2 study of 219 subjects with complicated skin and skin structure infection (cSSSI) and a sponsor-terminated Phase 3 study of 140 subjects with cSSSI. Omadacycline was well-tolerated and demonstrated efficacy similar to an established comparator (linezolid).

In a recently completed global Phase 3 study of 645 subjects comparing the safety and efficacy of intravenous (i.v.) and per oral (p.o.) omadacycline to i.v. and p.o. linezolid in the treatment of adult subjects with ABSSSI, omadacycline was non-inferior to linezolid and was well tolerated.

I. Study Design

This was a Phase 3 study designed to demonstrate the safety and efficacy of p.o. omadacycline as compared to p.o. linezolid in the treatment of adult subjects with ABSSSI. Specifically, the study was designed to demonstrate that omadacycline administered orally (p.o.) for 7 to 14 days is (10%) non-inferior to linezolid administered orally for 7 to 14 days in the treatment of adult subjects with ABSSSI known or suspected to be due to Gram-positive pathogens. In addition, the study was designed to demonstrate that omadacycline is safe in treating adult subjects with ABSSSI; and that the observed Clinical Response is due to neutralizing the identified causative pathogen of ABSSSI. Finally, the pharmacokinetics (PK) of oral omadacycline was evaluated in these in adult subjects.

The experiment was designed as a randomized (1:1), double-blind, double-dummy, active comparator-controlled, Phase 3 study comparing omadacycline and linezolid for the treatment of adult subjects with ABSSSI that was known or suspected to be due to a Gram-positive pathogen(s). Enrollment of subjects with major abscess may be up to 30% of randomized subjects. Enrollment of subjects who had received a single dose of an allowed short-acting antibiotic within the 72 hours prior to randomization were limited to no more than 25% of randomized subjects. Subject randomization was stratified across treatment groups by type of infection (wound infection, cellulitis/erysipelas, or major abscess) and receipt of a prior allowed short-acting antibiotic (yes or no).

The study consisted of 3 protocol-defined phases: Screening, Double-Blind Treatment, and Follow-up. All Screening evaluations, with the exception of the blood culture, was completed within the 24 hours prior to randomization. The blood culture was completed within the 24 hours prior to the first dose of test article. Subjects who met inclusion criteria, and did not meet exclusion criteria, were randomly assigned to a treatment group, and received their first dose of test article (either omadacycline or linezolid) at the site within 4 hours after randomization.

The study was designed in accordance with the U.S. FDA and European Medicines Agency (EMA) guidance on developing antimicrobial drugs for the treatment of ABSSSI, in addition to the guidelines of the Infectious Diseases Society of America (IDSA) and 2012 Update from the Biomarkers Consortium of the Foundation for the National Institutes of Health.

The comparator drug, linezolid, has been approved worldwide for the treatment of ABSSSI caused by Gram-positive pathogens and has an acceptable and well-defined safety profile. Linezolid can be administered orally, and has regulatory approval for the treatment of ABSSSI caused by Gram-positive pathogens including MRSA.

Subjects participated in the study for approximately 30 days. Following Screening, eligible subjects were randomly assigned to receive 7 to 14 days of p.o. treatment with either omadacycline or linezolid. A follow-up office visit occurred approximately 7 to 14 days after the last dose of test article, and a follow-up telephone contact occurred approximately 30 to 37 days after the first dose of test article.

To be eligible for randomization in this study, other than informed consent, an eligible subject fulfilled all of the following key criteria: (1) male or female, age 18 years or older; (2) had a qualifying skin and skin structure infection. For the purpose of the clinical trial, all qualifying lesions were greater than or equal to 75 $cm^2$ in total surface area of contiguous involved tissue, calculated as the product of the maximum length (head-to-toe) multiplied by the maximum width (measured perpendicular to length) as measured by the investigator using a wound ruler. Involved tissue was defined as tissue exhibiting clear evidence of one or more of the following: erythema, edema or induration; (3) the classification of qualifying infections was: wound infection—an infection characterized by purulent drainage from a wound with surrounding erythema, edema, and/or induration extending at least 5 cm in the shortest distance from the peripheral margin of the wound; Cellulitis/erysipelas—a diffuse skin infection characterized by spreading areas of erythema, edema, and/or induration; Major abscess—an infection characterized by a collection of pus within the dermis or deeper with surrounding erythema, edema, and/or induration extending at least 5 cm in the shortest distance from the peripheral margin of the abscess; (4) had evidence of a systemic inflammatory response within the 24 hours prior to randomization, as indicated by ONE of the following: elevated white blood cell (WBC) count (greater than or equal to 10,000 cells/$mm^3$) or leukopenia (less than or equal to 4,000 cells/$mm^3$); elevated immature neutrophils (greater than or equal to 15% band forms) regardless of total peripheral WBC count; lymphatic involvement: lymphangitis or lymphadenopathy that was proximal to and in a location that suggested drainage from the qualifying infection; and fever or hypothermia documented by the investigator (temperature greater than 38.0° C. [100.4° F.] or less than 36.0° C. [95.5° F.]).

During the screening phase, subject eligibility and baseline characteristics (based on a comprehensive history and physical examination, paying particular attention to medical history relating to the infection under study) for each subject were established. Subjects were eligible for Screening if they presented with ABSSSI signs and symptoms. For example, at the screening evaluation, the type of ABSSSI was recorded: wound infection, cellulitis/erysipelas or major abscess as defined in the inclusion criteria. To qualify, there must be greater than or equal to 75 $cm^2$ in total surface area of contiguous involved tissue (i.e., surrounding erythema, edema and/or induration).

The anatomical location of the primary site of infection was also recorded. For subjects with multiple non-contiguous areas of infection, the most severely affected portion was identified at Screening and was designated as the primary lesion site. The presence and nature of any foreign body (e.g., wood, metal, plastic, etc.) present at the site of infection was noted. The following information regarding the primary site of infection was recorded: presence of lymphadenopathy proximal to primary lesion site; and presence of lymphangitis proximal to primary lesion site; presence of drainage from the primary lesion site and description (serous/serosanguineous, seropurulent, or purulent). Semi-quantitative (none, mild, moderate, severe) description of infection for the following features was also provided: tenderness, edema, erythema, & induration.

The Screening evaluation measurement of lesion size was collected within 4 hours prior to randomization. Surface area of lesions was calculated by multiplying the head-to-toe maximum length of the total lesion and maximum width (perpendicular to maximum length) inclusive of contiguous involvement (erythema, edema and/or induration). Investigator ruler measurements could be used to document the lesion size.

In addition, each subject was asked to report certain outcomes or parameters related to disease status and treatment efficacy, such as Numerical Rating Scale for Pain (0-10) at the primary ABSSSI lesion site; SF-36v2® Health Survey (which was referred to as a generic health survey because it can be used across age (18 and older), disease, and treatment group, as opposed to a disease-specific health survey, which focuses on a particular condition or disease). In addition, a urine dipstick was performed locally at Screening.

Subjects who met inclusion criteria, and did not meet exclusion criteria were randomly assigned to a treatment group, and received their first dose of test article at the site within 4 hours after randomization.

Subjects were randomized (1:1) to 1 of the following 2 treatment arms:

Investigational therapy: omadacycline, 450 mg p.o. every 24 hours (q24h) for 2 doses, followed by 300 mg p.o. q24h. Total treatment duration of 7 to 14 days.

Reference therapy: linezolid, 600 mg p.o. every 12 hours (q12h). Total treatment duration of 7 to 14 days.

The study employed a double-blind, double-dummy design using omadacycline placebo comparator tablets of matching size and shape to active omadacycline tablets and matching over-encapsulated placebo and over-encapsulated active linezolid tablets. To maintain double blinding, subjects on both arms received the same number of tablets.

The double-blind treatment period, according to the instant Experiment, was designed to be 7 to 14 days in duration. The following table summarizes actual study drug exposure in the safety population:

| Characteristics | Omadacycline (N = 368) n (%) | Linezolid (N = 367) n (%) |
| --- | --- | --- |
| Duration of exposure on therapy (days) | | |
| n | 368 | 367 |
| Mean (SD) | 8.2 (2.77) | 8.0 (2.98) |
| Median | 8.0 | 7.0 |
| Min, Max | 1, 14 | 1, 17 |
| Duration of exposure on therapy (days), n (%) | | |
| n | 368 | 367 |
| 1-3 | 30 (8.2) | 40 (10.9) |
| 4-6 | 11 (3.0) | 12 (3.3) |
| 7-10 | 286 (77.7) | 278 (75.7) |

-continued

| Characteristics | Omadacycline (N = 368) n (%) | Linezolid (N = 367) n (%) |
| --- | --- | --- |
| 11-12 | 12 (3.3) | 6 (1.6) |
| 13-14 | 29 (7.9) | 26 (7.1) |
| >14 | 0 | 5 (1.4) |

Percentages for duration of exposure were based on subjects receiving at least one dose.
Duration of study drug exposure in days = date of last dose − date of first dose + 1.

All doses of test article were taken with water. There were fasting requirements for administration of the odd numbered doses due to effects of food on oral omadacycline. These fasting requirements were considered when determining the time of day when subjects took their doses.

II. Efficacy and Evaluation

Subjects were evaluated at 2 visits after the completion of treatment: at the PTE (Post Therapy Evaluation) visit, 7 to 14 days after the subject's last day of study therapy, and at a Final Follow-up assessment, 30 to 37 days after the first dose of treatment. The Final Follow-up assessment could be conducted via telephone contact or by another interactive technology for subjects who were considered to be Clinical Successes and had no AEs or clinically significant laboratory or ECG abnormalities noted at or after the PTE visit. Otherwise, this assessment was performed with an in person study visit.

Efficacy analysis was based on the following list of key assessments:
Clinical assessment of the site of infection
Assessment of lesion size
Assessment of the need for adjunct surgical procedures
Microbiological assessment of the infection
Assessment of clinical response by the investigator
Assessment of all-cause mortality
Each is described in further detail below.

a. Clinical Assessment of the Site of Infection

The clinical assessment of the site of infection was conducted at Screening and every scheduled evaluation with the exception of the Final Follow-up assessment. A clinical assessment of the site of infection was performed within 48 to 72 hours after the first dose. The primary site of infection was examined, and the following information was recorded: presence of drainage from the primary lesion site and description (serous/serosanguineous, seropurulent, or purulent); and semi-quantitative (none, mild, moderate, severe) description of infection for the following features—tenderness; edema; erythema; and induration.

b. Assessment of Lesion Size

Lesion measurements by ruler was performed at Screening, and every scheduled evaluation with the exception of the Final Follow-up assessment.

Surface area of lesions was calculated by multiplying the head-to-toe maximum length of total lesion and maximum width (perpendicular to maximum length) inclusive of contiguous involvement (erythema, edema and/or induration). Investigator ruler measurements were used to document lesion size.

c. Microbiological Assessment of the Site of Infection

At the Screening visit, material was collected from the site of infection and submitted to site's local microbiology laboratory for Gram stain and culture. The type of specimen submitted was recorded. Laboratory reports on Gram stains included a semi-quantitative description of the number of polymorphonuclear leukocytes per low power field (i.e., 100×) and a description of bacteria seen. Blood cultures were also performed to assess concurrent bacteremia.

As the site of infection responded to therapy, repeated cultures may not be clinically appropriate and/or there may be no material for culture. At the EOT and/or PTE visit, infection site specimen cultures and Gram stains were obtained only for subjects who were clinical failures and require alternative antibacterial treatment for the infection under study.

All specimens submitted to the site's local laboratory were evaluated for aerobic and, where appropriate, anaerobic culture. Culture results included a semi-quantitative description of the organisms on the primary culture plate and identification of all isolates to the level of genus and species. Susceptibility testing for linezolid was performed locally using a standard method chosen by the laboratory. Results of this testing were used along with clinical findings to help guide therapy.

All bacterial isolates identified from infection site specimens or blood were submitted to the Central Laboratory for verification of genus and species and for standardized minimum inhibitory concentration (MIC) testing performed for omadacycline, linezolid and a panel of currently approved antibiotics.

If there was evidence of a Gram-negative or anaerobic microorganism, or microorganism that was non-susceptible to linezolid, the decision to continue or discontinue test article and change the antibacterial regimen was made based on the investigator's clinical judgment and were recorded in the source documents.

d. Assessment of Clinical Outcome

Assessment of clinical outcome occurred at the Early Clinical Response assessment (programmatically), EOT, and PTE as described below.

i) Evaluation of the Infection Under Study at the Early Clinical Response Assessment The formal determination of the response to therapy at the Early Clinical Response assessment (48 to 72 hours after the first dose of test article) was done programmatically using lesion measurement values.

"Clinical Success" at the Early Clinical Response assessment was defined as meeting all 3 of the following: the subject was alive; the size of the primary lesion had been reduced greater than or equal to 20% compared to Screening measurements, without receiving any alternative (rescue) antibacterial therapy; and the subject did not meet any criteria for Clinical Failure or Indeterminate (see below for definitions).

"Clinical Failure" was defined as meeting any of the criteria below: the size of the primary lesion had not been reduced by greater than or equal to 20% compared to Screening measurements; test article was discontinued based on the determination that the infection had responded inadequately such that alternative (rescue) antibacterial therapy was needed; the subject received antibacterial therapy that may be effective for the infection under study for a different infection from the one under study; the subject developed an AE that required discontinuation of test article prior to the Early Clinical Response assessment and alternative (rescue) antibacterial therapy was needed; or death prior to Early Clinical Response assessment.

"Indeterminate" was given when the clinical response to test article could not be adequately inferred because: subject was not seen for Early Clinical Response assessment because they withdrew consent, were lost to follow-up, or other reasons.

ii) Clinical Evaluation of the Infection Under Study at EOT

At the EOT visit (on the day of or within 2 days following the last dose of test article), the clinical status of the infection under was indicated as detailed below.

"Clinical Success" at the End of Treatment (EOT) assessment was defined as meeting the following: the subject was alive; and the infection was sufficiently resolved such that further antibacterial therapy was not needed (these subjects might have some residual changes related to infection requiring ancillary (i.e., non-antibiotic) treatment, e.g., bandages on a healing wound, debridement of uninfected tissue (i.e., necrotic)).

Clinical Failure was defined as meeting any of the criteria below, the primary reason for clinical failure was designated: test article was discontinued based on the determination that the infection had responded inadequately such that alternative (rescue) antibacterial therapy was needed; the subject received antibacterial therapy that may be effective for the infection under study for a different infection from the one under study; or the subject developed an AE that required discontinuation of test article prior to completion of the planned test article regimen and alternative (rescue) antibacterial therapy was needed; unplanned major surgical intervention (i.e., procedures that would not normally be performed at the bedside) for the infection under study; the subject died before evaluation; or others.

"Indeterminate" was given if the clinical response to test article could not be adequately inferred. All that apply are marked: The subject was not seen for EOT assessment because they withdrew consent, were lost to follow-up, or other reason.

iii) Clinical Evaluation of the Infection Under Study at PTE

At the Post Therapy Evaluation PTE visit (7 to 14 days after the subject's last day of study therapy), ONE of the following outcomes relating to the primary infection under study was indicated:

"Clinical Success" at the Post Therapy Evaluation assessment was defined as meeting the following: the subject was alive; the infection was sufficiently resolved such that further antibacterial therapy was not needed (these subjects might have some residual changes related to infection requiring ancillary (i.e., non-antibiotic) treatment, e.g., bandages on a healing wound, debridement of uninfected tissue (i.e., necrotic).

"Clinical Failure" was defined as meeting any of the criteria below, the primary reason for clinical failure was designated: the infection required additional treatment with alternative (rescue) antibacterial therapy; the subject received antibacterial therapy between EOT and PTE that may be effective for the infection under study for a different infection from the one under study; unplanned major surgical intervention (i.e., procedures that would not normally be performed at the bedside) for the infection under study between EOT and PTE; the subject died before evaluation; and others.

"Indeterminate" was given when the clinical response to test article could not be adequately inferred. All that apply were marked: the subject was not seen for PTE assessment because they withdrew consent, were lost to follow-up, and other reason.

III. Pharmacokinetic Studies

PK data was analyzed using a population PK model. Blood samples were collected for PK analysis using a sparse sampling method for the population PK model. The number of samples and collection schedule vary for individual subjects. Up to 4 blood samples were collected per subject between Days 2 and 3. Blood was collected either by fresh venipuncture or via a cannula used solely for that purpose. The dates and times for all doses of test article and PK sample collections were recorded. The identification of the subject, sample number and the time of the sample collection to the nearest minute were immediately recorded on the collection tube. The tube was centrifuged at 1500×g for 10 minutes; the separated plasma transferred in 2 equal aliquots into pre-labeled tubes; and the tubes frozen at −70° C. within 60 minutes of collection. The time the sample was frozen was recorded to the nearest minute.

The samples for omadacycline were analyzed using a specific, sensitive and validated Liquid Chromatography/Tandem Mass Spectrometry (LC/MS/MS) method.

IV. Safety Monitoring

An Adverse Event (AE) is any untoward, undesired, or unplanned event in the form of signs, symptoms, disease, or laboratory or physiologic observations occurring in a person given a test article or in a clinical study. The event does not need to be causally related to the test article or clinical study. An AE includes, but is not limited to, the following: any clinically significant worsening of a preexisting condition; an AE occurring from overdose of a test article, whether accidental or intentional; overdose is a dose greater than that specified in the protocol; an AE occurring from abuse (e.g., use for nonclinical reasons) of a test article; and an AE that has been associated with the discontinuation of the use of a test article.

The severity (or intensity) of an AE was classified using the following criteria:

Mild: These events were usually transient, required minimal or no treatment, and did not interfere with the subject's daily activities.

Moderate: These events resulted in a low level of inconvenience or concern with the therapeutic measures. Moderate events might cause some interference with normal functioning but posed no significant or permanent risk of harm.

Severe: These events interrupted a subject's usual daily activity and might require systemic drug therapy or other treatment. Severe events were usually incapacitating.

A Serious Adverse Event (SAE) is an AE that: resulted in death; was life-threatening (see below); required hospitalization or prolongation of an existing hospitalization (see below); resulted in a persistent or significant disability or incapacity (see below); resulted in a congenital anomaly or birth defect; additionally, important medical events that may not result in death, be life-threatening, or require hospitalization may be considered SAEs when, based on appropriate medical judgment, they might jeopardize the subject and might require medical or surgical intervention to prevent any one (1) of the outcomes listed above in this definition. Examples of such events include allergic bronchospasm requiring intensive treatment in an emergency room or at home, blood dyscrasias or convulsions that do not result in hospitalization, or development of drug dependency or drug abuse.

Life-threatening refers to immediate risk of death as the event occurred per the reporter. A life-threatening experience did not include an experience, had it occurred in a more severe form, might have caused death, but as it actually occurred, did not create an immediate risk of death.

Hospitalization is official admission to a hospital. Hospitalization or prolongation of a hospitalization constitutes criteria for an AE to be serious; however, it is not in itself considered an SAE. In absence of an AE, a hospitalization or prolongation of a hospitalization was not reported as an SAE by the participating investigator. This was the case in the following situations: the hospitalization or prolongation of hospitalization was needed for a procedure required by the protocol; the hospitalization or prolongation of hospitalization was part of a routine procedure followed by the center (e.g., stent removal after surgery); and a hospitalization for a preexisting condition that had not worsened.

Disability is defined as a substantial disruption in a person's ability to conduct normal life functions. If there was any doubt about whether the information constitutes an SAE, the information was treated as an SAE.

A subject's AEs and SAEs were recorded and reported from the signing of the Informed Consent Form to the time of the Final Follow-up assessment. The subject was instructed to report AEs and SAEs during this time period. Reports of death within 30 days after the last contact with the subject was reported to the sponsor and additional information relative to the cause of death was sought and documented.

The subjects were followed-up as medically necessary on all AEs and SAEs until the events had subsided, the condition had returned to Baseline, or in case of permanent impairment, until the condition stabilized.

AEs were based on the signs or symptoms detected during the physical examination and on clinical evaluation of the subject. If an AE required a surgical or diagnostic procedure, the illness leading to the procedure was recorded as the AE, not the procedure itself. Death was recorded as an outcome of an AE. Any unanticipated risks to the subjects were reported promptly.

Concerning relatedness, causality (i.e., whether there was a reasonable possibility that test article caused the event) for all AEs and SAEs was assessed. The relationship was characterized using the following classification:

Not related: This relationship suggested that there was no association between test article and the reported event. The event could be explained by other factors such as an underlying medical condition, concomitant therapy, or accident, and no plausible temporal or biologic relationship existed between test article and the event.

Related: This relationship suggested that a definite causal relationship existed between test article administration and the AE, or there was a reasonable possibility that the event was caused by the study medication, and other conditions (concurrent illness, progression/expression of disease state, or concurrent medication reaction) did not appear to explain the event.

AEs and SAEs were also assessed for their potential relationship to the protocol. A protocol-related adverse event was one that was not related to the test article, but was considered by the investigator or the medical monitor (or designee) to be related to the research conditions, i.e., related to the fact that a subject was participating in the study. For example, a protocol-related AE might be an untoward event related to a medical procedure required by the protocol.

The severity (or intensity) of an AE was classified using the following criteria:

Mild: These events were usually transient, required minimal or no treatment, and did not interfere with the subject's daily activities.

Moderate: These events resulted in a low level of inconvenience or concern with the therapeutic measures. Moderate events might cause some interference with normal functioning but posed no significant or permanent risk of harm.

Severe: These events interrupted a subject's usual daily activity and may require systemic drug therapy or other treatment. Severe events were usually incapacitating.

Changes in the severity of an AE was documented as a new event to allow an assessment of the duration of the event at each level of intensity to be performed.

Protocol-defined safety laboratory test results were analyzed as part of specific laboratory safety analyses. Additional laboratory test results at other time points might be available as part of standard clinical practice. Throughout the study, laboratory-related abnormalities were recorded as AEs only if considered clinically significant, outside the range of expected values given the subject's baseline assessments and clinical course, and not known to be part of another AE diagnosis.

The skin infection that qualified the subject for entry in the study ("qualifying ABSSSI") was unique because data regarding the progress of this infection were being captured as part of efficacy analyses. Therefore, worsening or progression of the qualifying ABSSSI was recorded as a clinical failure (as part of the efficacy assessment), rather than an AE, unless the worsening/progression also met the criteria for a serious AE (in which case the event also was reported as an SAE). In contrast, any new or secondary infections that the investigator considered to be distinct from the qualifying ABSSSI (e.g., a secondary skin abscesses in a different anatomical location) was reported as AEs in all cases, whether non-serious or serious.

V. Data Analysis

All analyses of data complied with International Conference on Harmonization of Technical Requirements for Registration of Pharmaceuticals for Human Use (ICH-E9) and the sponsor's guidance documents and standards. Statistical analyses were performed using Statistical Analysis Software (SAS).

A SAP incorporating the sections below and with mock table, figure and listing (TFL) shells was prepared prior to the start of the study. This plan defined populations for analysis, outlined all data handling conventions and specified statistical methods to be used for analysis of safety and efficacy. As a consequence of differing regulatory requirements for the choice of the primary efficacy outcome and statistical analyses, 2 separate SAPs were prepared (one each for FDA and EMA). The sections below indicate the overall structure and approach of the analyses.

Inferential statistical analyses of the primary and secondary outcomes were conducted as outlined below. Descriptive statistics, including the numbers and percentages for categorical variables, and the numbers, means, standard deviations (SD), medians, minimums, and maximums for continuous variables were provided. All comparisons were for omadacycline versus linezolid. Exploratory analyses might also be performed. Listings of individual subject's data were produced.

Analysis Populations

A number of subject analysis populations had been defined for the various analyses of efficacy and safety, as follows:

The intent-to-treat (ITT) population consisted of all randomized subjects.

The safety population consisted of all randomized subjects who received test article.

The modified intent-to-treat (mITT) population consisted of all randomized subjects without a sole Gram-negative causative pathogen(s) at Screening.

The microbiological modified intent-to-treat (micromITT) population consisted of subjects in the mITT population who had at least 1 Gram-positive causative pathogen (s) at Screening (e.g., bacterial pathogen identified from a blood culture or from a culture of a microbiological sample obtained from the primary ABSSSI site at baseline).

The clinically evaluable (CE) population (CE-PTE and CE-EOT) consisted of all mITT subjects who received at least one dose of test article, had a qualifying ABSSSI, an investigator's assessment of clinical response at the PTE/EOT visit, with no indeterminate clinical response, and met specific criteria related to the required assessments.

The microbiologically evaluable (ME) population included subjects in the CE population who had at least 1 Gram-positive causative pathogen(s) at Screening (i.e., all subjects in both the micro-mITT and the CE-PTE/EOT populations).

The various subject populations participated in the study, as defined above, are summarized below:

| Population | Omadacycline n (%) | Linezolid n (%) | All Subjects n (%) |
| --- | --- | --- | --- |
| ITT | 368 | 367 | 735 |
| Safety | 368 (100.0) | 367 (100.0) | 735 (100.0) |
| mITT | 360 (97.8) | 360 (98.1) | 720 (98.0) |
| micro-mITT | 276 (75.0) | 287 (78.2) | 563 (76.6) |
| CE-EOT | 304 (82.6) | 296 (80.7) | 600 (81.6) |
| CE-PTE | 284 (77.2) | 292 (79.6) | 576 (78.4) |
| ME-EOT | 233 (63.3) | 229 (62.4) | 462 (62.9) |
| ME-PTE | 220 (59.8) | 225 (61.3) | 445 (60.5) |

Subject disposition in the ITT population is summarized below:

| Parameter/Category | Omadacycline (N = 368) n (%) | Linezolid (N = 367) n (%) | All Subjects (N = 735) n (%) | p-value |
| --- | --- | --- | --- | --- |
| Randomized | 368 (100.0) | 367 (100.0) | 735 (100.0) | |
| Completed Study Treatment [1] | 328 (89.1) | 315 (85.8) | 643 (87.5) | |
| Prematurely Discontinued from Study Treatment | 40 (10.9) | 52 (14.2) | 92 (12.5) | 0.1829 |
| Reason For Premature Discontinuation from Study Treatment | | | | |
| Adverse Event | 6 (1.6) | 4 (1.1) | 10 (1.4) | |
| Lost to Follow-up | 18 (4.9) | 25 (6.8) | 43 (5.9) | |
| Withdrawal by Subject | 6 (1.6) | 8 (2.2) | 14 (1.9) | |
| Physician Decision | 3 (0.8) | 7 (1.9) | 10 (1.4) | |
| Death | 0 | 0 | 0 | |

| Parameter/Category | Omadacycline (N = 368) n (%) | Linezolid (N = 367) n (%) | All Subjects (N = 735) n (%) | p-value |
|---|---|---|---|---|
| Other | 7 (1.9) | 8 (2.2) | 15 (2.0) | |
| Completed Study [2] | 314 (85.3) | 310 (84.5) | 624 (84.9) | |
| Prematurely Discontinued from Study | 54 (14.7) | 57 (15.5) | 111 (15.1) | 0.7583 |
| Reason For Premature Discontinuation from Study | | | | |
| Adverse Event | 1 (0.3) | 0 | 1 (0.1) | |
| Lost to Follow-up | 37 (10.1) | 38 (10.4) | 75 (10.2) | |
| Withdrawal by Subject | 11 (3.0) | 12 (3.3) | 23 (3.1) | |
| Physician Decision | 0 | 1 (0.3) | 1 (0.1) | |
| Death | 0 | 0 | 0 | |
| Other | 5 (1.4) | 6 (1.6) | 11 (1.5) | |

* Percentages are based on the ITT population, p-values for differences between treatment groups are from Fisher's exact test.
[1] Subjects that completed the study treatment.
[2] Subjects that completed the study (i.e., received at least one dose of test article and completed EOT, PTE and Follow-up).

Subject disposition in the mITT population is summarized below:

| Parameter/Category | Omadacycline (N = 360) n (%) | Linezolid (N = 360) n (%) | All Subjects (N = 720) n (%) | p-value |
|---|---|---|---|---|
| Randomized | 360 (100.0) | 360 (100.0) | 720 (100.0) | |
| Completed Study Treatment[1] | 321 (89.2) | 309 (85.8) | 630 (87.5) | |
| Prematurely Discontinued from Study Treatment | 39 (10.8) | 51 (14.2) | 90 (12.5) | 0.2150 |
| Reason For Premature Discontinuation from Study Treatment | | | | |
| Adverse Event | 6 (1.7) | 4 (1.1) | 10 (1.4) | |
| Lost to Follow-up | 18 (5.0) | 25 (6.9) | 43 (6.0) | |
| Withdrawal by Subject | 5 (1.4) | 7 (1.9) | 12 (1.7) | |
| Physician Decision | 3 (0.8) | 7 (1.9) | 10 (1.4) | |
| Death | 0 | 0 | 0 | |
| Other | 7 (1.9) | 8 (2.2) | 15 (2.1) | |
| Completed Study[2] | 306 (85.0) | 304 (84.4) | 610 (84.7) | |
| Prematurely Discontinued from Study | 54 (15.0) | 56 (15.6) | 110 (15.3) | 0.9175 |
| Reason For Premature Discontinuation from Study | | | | |
| Adverse Event | 1 (0.3) | 0 | 1 (0.1) | |
| Lost to Follow-up | 37 (10.3) | 38 (10.6) | 75 (10.4) | |
| Withdrawal by Subject | 11 (3.1) | 11 (3.1) | 22 (3.1) | |
| Physician Decision | 0 | 1 (0.3) | 1 (0.1) | |
| Death | 0 | 0 | 0 | |
| Other | 5 (1.4) | 6 (1.7) | 11 (1.5) | |

*Percentages are based on the mITT population, p-values for differences between treatment groups are from Fisher's exact test.
[1]Subjects that completed the study treatment.
[2]Subjects that completed the study (i.e., received at least one dose of test article and completed EOT, PTE and Follow-up).

Subject disposition in the CE-PTE population is summarized below:

| Parameter/Category | Omadacycline (N = 284) n (%) | Linezolid (N = 292) n (%) | All Subjects (N = 576) n (%) | p-value |
|---|---|---|---|---|
| Randomized | 284 (100.0) | 292 (100.0) | 576 (100.0) | |
| Completed Study Treatment[1] | 277 (97.5) | 283 (96.9) | 560 (97.2) | |
| Prematurely Discontinued from Study Treatment | 7 (2.5) | 9 (3.1) | 16 (2.8) | 0.8012 |
| Reason For Premature Discontinuation from Study Treatment | | | | |
| Adverse Event | 3 (1.1) | 2 (0.7) | 5 (0.9) | |
| Lost to Follow-up | 1 (0.4) | 1 (0.3) | 2 (0.3) | |

-continued

| Parameter/Category | Omadacycline (N = 284) n (%) | Linezolid (N = 292) n (%) | All Subjects (N = 576) n (%) | p-value |
|---|---|---|---|---|
| Withdrawal by Subject | 0 | 1 (0.3) | 1 (0.2) | |
| Physician Decision | 1 (0.4) | 4 (1.4) | 5 (0.9) | |
| Death | 0 | 0 | 0 | |
| Other | 2 (0.7) | 1 (0.3) | 3 (0.5) | |
| Completed Study[2] | 275 (96.8) | 287 (98.3) | 562 (97.6) | |
| Prematurely Discontinued from Study | 9 (3.2) | 5 (1.7) | 14 (2.4) | 0.2899 |
| Reason For Premature Discontinuation from Study | | | | |
| Adverse Event | 1 (0.4) | 0 | 1 (0.2) | |
| Lost to Follow-up | 8 (2.8) | 4 (1.4) | 12 (2.1) | |
| Withdrawal by Subject | 0 | 1 (0.3) | 1 (0.2) | |
| Physician Decision | 0 | 0 | 0 | |
| Death | 0 | 0 | 0 | |
| Other | 0 | 0 | 0 | |

*Percentages are based on the CE-PTE population, p-values for differences between treatment groups are from Fisher's exact test.
[1]Subjects that completed the study treatment.
[2]Subjects that completed the study (i.e., received at least one dose of test article and completed EOT, PTE and Follow-up).

Demographic and baseline characteristics of the safety population is summarized below:

| Characteristics | Omadacycline (N = 368) | Linezolid (N = 367) | All Subjects (N = 735) | p-value |
|---|---|---|---|---|
| Gender n (%) | | | | |
| n | 368 | 367 | 735 | |
| Female | 126 (34.2) | 147 (40.1) | 273 (37.1) | |
| Male | 242 (65.8) | 220 (59.9) | 462 (62.9) | 0.109 |
| Race n (%) | | | | |
| n | 368 | 367 | 735 | |
| White | 327 (88.9) | 341 (92.9) | 668 (90.9) | |
| Black or African American | 22 (6.0) | 13 (3.5) | 35 (4.8) | |
| Asian | 3 (0.8) | 5 (1.4) | 8 (1.1) | |
| American Indian or Alaska Native | 7 (1.9) | 3 (0.8) | 10 (1.4) | |
| Native Hawaiian or Other Pacific Islander | 3 (0.8) | 0 | 3 (0.4) | |
| Other | 6 (1.6) | 5 (1.4) | 11 (1.5) | 0.176 |
| Ethnicity n (%) | | | | |
| n | 368 | 367 | 735 | |
| Hispanic or Latino | 154 (41.8) | 156 (42.5) | 310 (42.2) | |
| Not Hispanic or Latino | 214 (58.2) | 211 (57.5) | 425 (57.8) | |
| Not Reported/Unknown | 0 | 0 | 0 | 0.881 |
| Age (years) | | | | |
| n | 368 | 367 | 735 | |
| Mean (SD) | 42.8 (12.72) | 44.5 (13.11) | 43.7 (12.94) | |
| Median | 41.0 | 46.0 | 43.0 | |
| Min, Max | 18, 86 | 20, 84 | 18, 86 | 0.109 |
| Categorical Age(years) n (%) | | | | |
| n | 368 | 367 | 735 | |
| 18-45 | 213 (57.9) | 183 (49.9) | 396 (53.9) | |
| >45-65 | 141 (38.3) | 164 (44.7) | 305 (41.5) | |
| >65-75 | 11 (3.0) | 12 (3.3) | 23 (3.1) | 0.131 |
| >75 | 3 (0.8) | 8 (2.2) | 11 (1.5) | |
| Height (cm) | | | | |
| n | 368 | 367 | 735 | |
| Mean (SD) | 171.33 (10.020) | 169.45 (9.745) | 170.39 (9.922) | |
| Median | 171.00 | 170.00 | 170.20 | |
| Min, Max | 137.0, 196.9 | 132.1, 193.0 | 132.1, 196.9 | 0.018 |
| Weight (kg) | | | | |
| n | 368 | 367 | 735 | |
| Mean (SD) | 81.62 (18.286) | 80.15 (19.778) | 80.89 (19.047) | |

-continued

| Characteristics | Omadacycline (N = 368) | Linezolid (N = 367) | All Subjects (N = 735) | p-value |
|---|---|---|---|---|
| Median | 79.40 | 76.20 | 77.70 | |
| Min, Max | 41.7, 167.0 | 44.5, 156.3 | 41.7, 167.0 | 0.074 |
| BMI (kg/m^2) | | | | |
| n | 368 | 367 | 735 | |
| Mean (SD) | 27.91 (6.472) | 27.93 (6.556) | 27.92 (6.510) | |
| Median | 26.71 | 26.54 | 26.64 | |
| Min, Max | 16.3, 71.3 | 16.7, 54.1 | 16.3, 71.3 | 0.911 |
| Renal Function (Central Lab) n (%) | | | | |
| n | 365 | 363 | 728 | |
| Normal renal function [CrCl >80 mL/min] | 343 (94.0) | 340 (93.7) | 683 (93.8) | |
| Mild renal impairment [CrCl >50-80 mL/min] | 21 (5.8) | 17 (4.7) | 38 (5.2) | |
| Moderate renal impairment [CrCl 30-50 mL/min] | 1 (0.3) | 6 (1.7) | 7 (1.0) | |
| Severe renal impairment [CrCl <30 mL/min] | 0 | 0 | 0 | 0.156 |

Age is calculated from the date of birth to the informed consent date.
p-values for differences between treatment groups are from Fisher's exact test (for categorical variables) or Wilcoxon Rank Sum test (for continuous variables).
For each categorical parameter, the denominator for the percentage is the number of subjects who had that parameter assessed.
CrCl = Creatinine clearance Demographic and baseline characteristics of the mITT population is summarized below:

| Characteristics | Omadacycline (N = 360) | Linezolid (N = 360) | All Subjects (N = 720) | p-value |
|---|---|---|---|---|
| Gender n (%) | | | | |
| n | 360 | 360 | 720 | |
| Female | 121 (33.6) | 145 (40.3) | 266 (36.9) | |
| Male | 239 (66.4) | 215 (59.7) | 454 (63.1) | 0.076 |
| Race n (%) | | | | |
| n | 360 | 360 | 720 | |
| White | 320 (88.9) | 334 (92.8) | 654 (90.8) | |
| Black or African American | 22 (6.1) | 13 (3.6) | 35 (4.9) | |
| Asian | 3 (0.8) | 5 (1.4) | 8 (1.1) | |
| American Indian or Alaska Native | 7 (1.9) | 3 (0.8) | 10 (1.4) | |
| Native Hawaiian or Other Pacific Islander | 3 (0.8) | 0 | 3 (0.4) | |
| Other | 5 (1.4) | 5 (1.4) | 10 (1.4) | 0.183 |
| Ethnicity n (%) | | | | |
| n | 360 | 360 | 720 | |
| Hispanic or Latino | 148 (41.1) | 151 (41.9) | 299 (41.5) | |
| Not Hispanic or Latino | 212 (58.9) | 209 (58.1) | 421 (58.5) | |
| Not Reported/Unknown | 0 | 0 | 0 | 0.880 |
| Age (years) | | | | |
| n | 360 | 360 | 720 | |
| Mean (SD) | 42.7 (12.60) | 44.5 (13.18) | 43.6 (12.92) | |
| Median | 41.0 | 45.5 | 43.0 | |
| Min, Max | 18, 86 | 20, 84 | 18, 86 | 0.101 |
| Categorical Age (years) n (%) | | | | |
| n | 360 | 360 | 720 | |
| 18-45 | 210 (58.3) | 180 (50.0) | 390 (54.2) | |
| >45-65 | 137 (38.1) | 160 (44.4) | 297 (41.3) | |
| >65-75 | 10 (2.8) | 12 (3.3) | 22 (3.1) | 0.123 |
| >75 | 3 (0.8) | 8 (2.2) | 11 (1.5) | |
| Height (cm) | | | | |
| n | 360 | 360 | 720 | |
| Mean (SD) | 171.38 (10.103) | 169.43 (9.740) | 170.41 (9.964) | |

| Characteristics | Omadacycline (N = 360) | Linezolid (N = 360) | All Subjects (N = 720) | p-value |
|---|---|---|---|---|
| Median | 171.00 | 170.00 | 170.20 | |
| Min, Max | 137.0, 196.9 | 132.1, 193.0 | 132.1, 196.9 | 0.014 |
| Weight (kg) | | | | |
| n | 360 | 360 | 720 | |
| Mean (SD) | 81.45 (18.233) | 80.25 (19.884) | 80.85 (19.073) | |
| Median | 79.30 | 76.60 | 77.70 | |
| Min, Max | 41.7, 167.0 | 44.5, 156.3 | 41.7, 167.0 | 0.116 |
| BMI (kg/m^2) | | | | |
| n | 360 | 360 | 720 | |
| Mean (SD) | 27.82 (6.407) | 27.96 (6.576) | 27.89 (6.488) | |
| Median | 26.68 | 26.59 | 26.65 | |
| Min, Max | 16.3, 71.3 | 16.7, 54.1 | 16.3, 71.3 | 0.916 |
| Renal Function (Central Lab) n (%) | | | | |
| n | 357 | 356 | 713 | |
| Normal renal function [CrCl >80 mL/min] | 338 (94.7) | 333 (93.5) | 671 (94.1) | |
| Mild renal impairment [CrCl >50-80 mL/min] | 18 (5.0) | 17 (4.8) | 35 (4.9) | |
| Moderate renal impairment [CrCl 30-50 mL/min] | 1 (0.3) | 6 (1.7) | 7 (1.0) | |
| Severe renal impairment [CrCl <30 mL/min] | 0 | 0 | 0 | 0.215 |

Age is calculated from the date of birth to the informed consent date.
p-values for differences between treatment groups are from Fisher's exact test (for categorical variables) or Wilcoxon Rank Sum test (for continuous variables).
For each categorical parameter, the denominator for the percentage is the number of subjects who had that parameter assessed.
CrCl = Creatinine clearance The primary ABSSSI infection site at baseline in the mITT population is summarized below:

| Characteristics | Omadacycline (N = 360) n (%) | Linezolid (N = 360) n (%) |
|---|---|---|
| Type of Primary Infection[1] | 360 | 360 |
| Wound Infection | 210 (58.3) | 214 (59.4) |
| Cellulitis/erysipelas | 86 (23.9) | 84 (23.3) |
| Major Abscess | 64 (17.8) | 62 (17.2) |
| Location of Primary Infection | 360 | 360 |
| Scalp | 1 (0.3) | 1 (0.3) |
| Neck | 3 (0.8) | 3 (0.8) |
| Face | 2 (0.6) | 2 (0.6) |
| Chest | 7 (1.9) | 5 (1.4) |
| Abdomen | 12 (3.3) | 17 (4.7) |
| Back | 6 (1.7) | 8 (2.2) |
| Groin | 1 (0.3) | 3 (0.8) |
| Hand | 14 (3.9) | 10 (2.8) |
| Foot | 7 (1.9) | 13 (3.6) |
| Shoulder | 14 (3.9) | 6 (1.7) |
| Buttock | 33 (9.2) | 37 (10.3) |
| Axillary | 8 (2.2) | 6 (1.7) |
| Arm | 119 (33.1) | 125 (34.7) |
| Leg | 131 (36.4) | 118 (32.8) |
| Elbow | 2 (0.6) | 3 (0.8) |
| Knee | 1 (0.3) | 4 (1.1) |

Percentages are based on the number of subjects with the specific parameter assessed.
More than one location of the primary infection site is recorded if the infection covers multiple sites.
[1]Actual type of infection as reported on the eCRF.

The baseline pathogenic organisms from the ABSSSI site or blood culture by genus and species in the micro-mITT Population are summarized below:

| Baseline Pathogen | Omadacycline (N = 276) n (%) | Linezolid (N = 287) n (%) |
|---|---|---|
| Gram-positive organisms (aerobes) | 270 (97.8) | 278 (96.9) |
| Staphylococcus aureus | 220 (79.7) | 233 (81.2) |
| MRSA | 104 (37.7) | 107 (37.3) |
| MSSA | 120 (43.5) | 130 (45.3) |
| Staphylococcus lugdunensis | 5 (1.8) | 0 |
| Streptococcus pyogenes | 29 (10.5) | 16 (5.6) |
| Streptococcus anginosus group | 57 (20.7) | 45 (15.7) |
| Streptococcus anginosus | 27 (9.8) | 20 (7.0) |
| Streptococcus intermedius | 23 (8.3) | 24 (8.4) |
| Streptococcus constellatus | 9 (3.3) | 7 (2.4) |
| Enterococcus faecalis | 8 (2.9) | 12 (4.2) |
| VRE | 0 | 2 (0.7) |
| VSE | 7 (2.5) | 10 (3.5) |
| Enterococcus faecium | 1 (0.4) | 1 (0.3) |
| VSE | 1 (0.4) | 1 (0.3) |
| Streptococcus agalactiae | 2 (0.7) | 2 (0.7) |
| Streptococcus mitis | 1 (0.4) | 0 |
| ... | | |
| Streptococcus viridans group | 3 (1.1) | 0 |
| Gram-positive organisms (anaerobes) | 17 (6.2) | 17 (5.9) |
| Clostridium perfringens | 5 (1.8) | 9 (3.1) |
| Finegoldia magna | 3 (1.1) | 1 (0.3) |
| ... | | |
| Gram-negative organisms (aerobes) | 24 (8.7) | 30 (10.5) |
| Enterobacter aerogenes | 0 | 1 (0.3) |
| Enterobacter cloacae | 5 (1.8) | 6 (2.1) |
| Escherichia coli | 4 (1.4) | 1 (0.3) |
| ... | | |
| Gram-negative organisms (anaerobes) | 11 (4.0) | 12 (4.2) |
| Prevotella denticola | 5 (1.8) | 1 (0.3) |
| Prevotella melaninogenica | 2 (0.7) | 3 (1.0) |

In the table above, percentages were based on the number of subjects in each treatment group. Subjects with the same pathogen isolated from multiple specimens were counted only once for that pathogen. Subjects with the same pathogen identified from both the blood and primary ABSSSI cultures were counted only once. MRSA and MSSA were considered distinct pathogens; VRE and VSE were considered distinct pathogens. When per-subject counts of *Staphylococcus aureus* were presented, subjects with both MRSA and MSSA were counted only once. When per-subject counts of each *Enterococcus* species were presented, subjects with both VRE and VSE were counted only once. Only representative or the most abundant genus/species were shown.

Primary Efficacy Analysis

For all efficacy analyses, subject data was analyzed in the group to which the subject was randomized. For the primary analyses for both the FDA and EMA, subjects were analyzed in the stratum to which they were randomized.

The Early Clinical Response could be Clinical Success, Clinical Failure and Indeterminate (defined previously). An Indeterminate Response was included in the denominator for the calculation of the percentage of subjects with a Clinical Success in the mITT population and thus, was essentially considered as a Clinical Failure for the purpose of the primary analysis for the FDA.

Investigator's Assessment of Clinical Response at PTE Efficacy Variable was defined as Investigator's Assessment of Clinical Response at the PTE visit with outcomes of Clinical Success, Clinical Failure and Indeterminate (defined previously) in the mITT population and Clinical Success and Clinical Failure in the CE population. Subjects with a response of Clinical Failure at EOT were defined as a Clinical Failure at PTE. An Indeterminate Response was included in the denominator for the calculation of the percentage of subjects with a Clinical Success in the mITT population and thus, was essentially considered a Clinical Failure for the purpose of the primary analysis for the EMA.

To demonstrate the efficacy of omadacycline is non-inferior to linezolid in the treatment of adult subjects with ABSSSI, the following hypothesis was evaluated by analysis of the Clinical Success rates.

The null hypothesis and alternate hypothesis for the Early Clinical Response endpoint were assessed in the mITT population as follows:

$$H_o: \theta_T - \theta_C \le -\Delta$$

$$H_{ai}: \theta_T - \theta_C > -\Delta$$

Where the clinical success rate for the omadacycline regimen is θT and for linezolid is θC Δ is the non-inferiority (NI) margin and is 0.10.

Similar null and alternative hypotheses can be set up with Λ of 0.10 for the PTE endpoint. For the Early Clinical Response (FDA) endpoint, a 2-sided 95% confidence interval (CI) approach for the difference of clinical success rates (using the point estimate of the difference: omadacycline response proportion minus linezolid response proportion) was used to test for the NI of the omadacycline arm compared to the linezolid arm in the mITT population. The 95% CI was calculated using the unstratified method proposed by Miettinen and Nurminen. Omadacycline is considered non-inferior to linezolid if the lower bound of the CI is greater than −0.10 (i.e., −10%).

For Investigator's Assessment of Clinical Response at PTE (EMA) primary efficacy analyses in both the mITT and CE populations, a 2-sided 95% CI approach for the difference of clinical success rates (using the point estimate of the difference: omadacycline response proportion minus linezolid response proportion) were used to test for the NI of the omadacycline arm compared to the linezolid arm. The 95% CI was calculated using the stratified (for the randomization stratification factors) method proposed by Miettinen and Nurminen. Omadacycline is considered non-inferior to linezolid if the lower bound of the CI is greater than −0.10 (i.e., −10%).

Early Clinical Response and Investigator's Assessment of Clinical Response at PTE were tested separately and were not co-primary endpoints. The probability for approving an ineffective drug based on PTE efficacy is 2.5%, regardless of the result for the Early Clinical Response endpoint and vice versa. An adjustment would only be required if winning on at least 1 endpoint would result in global approval. In addition, no alpha adjustment is needed for the co-primary efficacy endpoints for the EMA (mITT and CE populations) since NI must be shown in both populations to conclude NI. Hence there was no adjustment for multiple endpoints.

Early clinical response at 48-72 hours after the first dose of the test articles (Omadacycline or linezolid) in the mITT population is summarized below:

| Efficacy Outcome | Omadacycline (N = 360) n (%) | Linezolid (N = 360) n (%) | Difference (95% CI) |
|---|---|---|---|
| Clinical Success | 315 (87.5) | 297 (82.5) | 5.0 (−0.2, 10.3) |
| Clinical Failure or Indeterminate | 45 (12.5) | 63 (17.5) | |
| Clinical Failure | 26 (7.2) | 32 (8.9) | |
| Indeterminate | 19 (5.3) | 31 (8.6) | |

In the table above, CI=Confidence Interval; Difference is observed difference in Early Clinical Success rate between the omadacycline and linezolid groups. 95% CI was constructed based on the Miettinen and Nurminen method without stratification. Percentages were based on the number of subjects in each treatment group.

Figure 6:
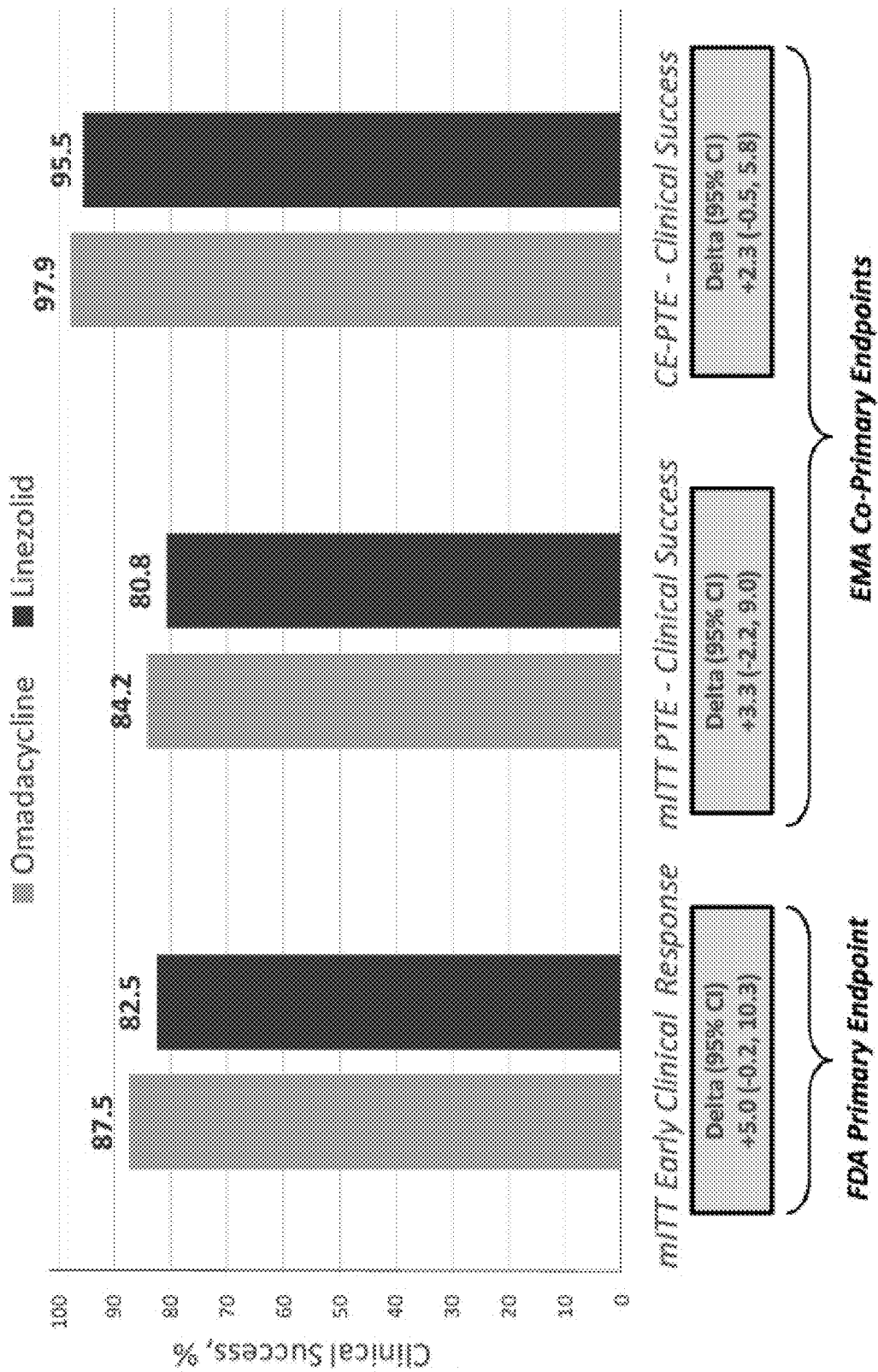
FIG. 6 shows that Omadacycline demonstrated statistical non-inferiority (10% margin) relative to linezolid, for early clinical response (ECR) in the mITT (modified Intent To Treat) population (see the pair of bars on the left) (FDA Primary Endpoint); and for clinical success at the PTE (Post Treatment/Therapy Evaluation), in both the mITT PTE population (see the middle pair of bars) and the CE-PTE (Clinically Evaluable population at the PTE) population (see the right pair of bars) (EMA Co-primary Endpoints).

The early clinical success rates (at 48-72 hrs) in the mITT population, for both Omadacycline and Linezolid, are depicted in FIG. 6. See the left most pair of bars. The data shows that the observed 5.0% difference in clinical success rate is well within the 10% margin of statistical non-inferiority between −0.2% and 10.3%, at 95% CI (Confidence Interval), and thus the primary efficacy point (for FDA approval) is met.

Early clinical response at 48-72 hours after the first dose of the test articles (Omadacycline or linezolid) by baseline pathogen from the ABSSSI site or blood culture in the micro-mITT population is summarized below:

| Baseline Pathogen | Omadacycline (N = 276) | | Linezolid (N = 287) | |
|---|---|---|---|---|
| | N1 | Clinical Success n (%) | N1 | Clinical Success n (%) |
| Gram-positive organisms (aerobes) | | | | |
| Staphylococcus aureus | 220 | 194 (88.2) | 233 | 194 (83.3) |
| MRSA | 104 | 97 (93.3) | 107 | 95 (88.8) |
| MSSA | 120 | 101 (84.2) | 130 | 103 (79.2) |
| Staphylococcus lugdunensis | 5 | 4 (80.0) | 0 | 0 |
| Streptococcus pyogenes | 29 | 24 (82.8) | 16 | 13 (81.3) |
| Streptococcus anginosus group | 57 | 54 (94.7) | 45 | 36 (80.0) |
| Streptococcus anginosus | 27 | 27 (100.0) | 20 | 17 (85.0) |
| Streptococcus intermedius | 23 | 21 (91.3) | 24 | 18 (75.0) |
| Streptococcus constellatus | 9 | 8 (88.9) | 7 | 7 (100.0) |
| Enterococcus faecalis | 8 | 7 (87.5) | 12 | 8 (66.7) |
| VRE | 0 | 0 | 2 | 2 (100.0) |
| VSE | 7 | 6 (85.7) | 10 | 6 (60.0) |
| Enterococcus faecium | 1 | 1 (100.0) | 1 | 1 (100.0) |
| VSE | 1 | 1 (100.0) | 1 | 1 (100.0) |
| Streptococcus agalactiae | 2 | 1 (50.0) | 2 | 1 (50.0) |
| Streptococcus mitis | 1 | 1 (100.0) | 0 | 0 |
| ... | | | | |
| Streptococcus viridans group | 3 | 3 (100.0) | 0 | 0 |
| Gram-positive organisms (anaerobes) | | | | |
| Clostridium perfringens | 5 | 5 (100.0) | 9 | 9 (100.0) |
| Finegoldia magna | 3 | 2 (66.7) | 1 | 0 (0.0) |
| ... | | | | |
| Gram-negative organisms (aerobes) | | | | |
| Enterobacter cloacae | 5 | 5 (100.0) | 6 | 5 (83.3) |
| Escherichia coli | 4 | 4 (100.0) | 1 | 1 (100.0) |
| Klebsiella pneumoniae | 5 | 4 (80.0) | 6 | 5 (83.3) |
| ... | | | | |
| Gram-negative organisms (anaerobes) | | | | |
| Prevotella denticola | 5 | 5 (100.0) | 1 | 1 (100.0) |
| Prevotella melaninogenica | 2 | 2 (100.0) | 3 | 3 (100.0) |
| ... | | | | |

In the table above, N1=Number of subjects in the micro-mITT population in the treatment group with the baseline pathogen; n=Number of subjects in the specific category. Percentages were based on N1. Subjects with the same pathogen isolated from multiple specimens were counted only once for that pathogen. Subjects with the same pathogen identified from both the blood and primary ABSSSI cultures were counted only once. Percentages were based on the number of subjects with the indicated pathogen. Only representative or the most abundant genus/species are shown.

If the null hypothesis of inferiority is rejected for the Early Clinical Response in the mITT population and the observed success response proportion for omadacycline is larger than the observed proportion for linezolid, a formal statistical analysis of superiority is conducted. If the lower limit of the 2-sided 95% CI for the treatment difference is greater than 0%, omadacycline is considered superior to linezolid.

The primary efficacy outcome was assessed separately across the stratification factors of type of infection and receipt of allowed antibacterial therapy in the 72 hours prior to randomization stratum by treatment group. For each type of infection stratum and each prior antibacterial therapy stratum, a 2-sided 95% CI for the observed difference in Early Clinical Response rates was calculated for the mITT population. Additional subgroup analyses of the primary efficacy outcome may be conducted as descriptive analyses.

The results of these separate assessments across the stratification factors are summarized below.

Specifically, early clinical response at 48-72 hours after the first dose of the test articles (Omadacycline or linezolid) by type of infection in the mITT population is summarized below:

In the table below, CI=Confidence Interval; Difference is observed difference in Early Clinical Success rate between the omadacycline and linezolid groups. 95% CI within each type of infection was constructed based on the Miettinen and Nurminen method without stratification. Percentages were based on the number of subjects in each treatment group within each type of infection. [1] Actual type of infection=Type of infection recorded on eCRF.

| | Type of Infection as Randomized | | | Actual Type of Infection[1] | | |
|---|---|---|---|---|---|---|
| Type of Infection Efficacy Outcome | Omadacycline (N = 360) n (%) | Linezolid (N = 360) n (%) | Difference (95% CI) | Omadacycline (N = 360) n (%) | Linezolid (N = 360) n (%) | Difference (95% CI) |
| Wound Infection | 214 | 214 | | 210 | 214 | |
| Clinical Success | 190 (88.8) | 177 (82.7) | 6.1 (−0.6, 12.8) | 187 (89.0) | 177 (82.7) | 6.3 (−0.3, 13.1) |
| Clinical Failure or Indeterminate | 24 (11.2) | 37 (17.3) | | 23 (11.0) | 37 (17.3) | |
| Clinical Failure | 17 (7.9) | 16 (7.5) | | 17 (8.1) | 16 (7.5) | |
| Indeterminate | 7 (3.3) | 21 (9.8) | | 6 (2.9) | 21 (9.8) | |
| Cellulitis/erysipelas | 82 | 84 | | 86 | 84 | |
| Clinical Success | 65 (79.3) | 65 (77.4) | 1.9 (−10.8, 14.5) | 68 (79.1) | 65 (77.4) | 1.7 (−10.8, 14.3) |
| Clinical Failure or Indeterminate | 17 (20.7) | 19 (22.6) | | 18 (20.9) | 19 (22.6) | |
| Clinical Failure | 8 (9.8) | 12 (14.3) | | 8 (9.3) | 12 (14.3) | |
| Indeterminate | 9 (11.0) | 7 (8.3) | | 10 (11.6) | 7 (8.3) | |
| Major Abscess | 64 | 62 | | 64 | 62 | |
| Clinical Success | 60 (93.8) | 55 (88.7) | 5.0 (−5.4, 16.2) | 60 (93.8) | 55 (88.7) | 5.0 (−5.4, 16.2) |
| Clinical Failure or Indeterminate | 4 (6.3) | 7 (11.3) | | 4 (6.3) | 7 (11.3) | |
| Clinical Failure | 1 (1.6) | 4 (6.5) | | 1 (1.6) | 4 (6.5) | |
| Indeterminate | 3 (4.7) | 3 (4.8) | | 3 (4.7) | 3 (4.8) | |

Overall clinical response at PTE visit based on investigator assessments in the mITT and CE-PTE populations is summarized below:

| Population | Efficacy Outcome | Omadacycline n (%) | Linezolid n (%) | Difference | 95% CI without Stratification[1] | 95% CI with Stratification[2] |
|---|---|---|---|---|---|---|
| mITT | | (N = 360) | (N = 360) | | | |
| | Clinical Success | 303 (84.2) | 291 (80.8) | 3.3 | (−2.2, 8.9) | (−2.2, 9.0) |
| | Clinical Failure or Indeterminate | 57 (15.8) | 69 (19.2) | | | |
| | Clinical Failure | 12 (3.3) | 21 (5.8) | | | |
| | Indeterminate | 45 (12.5) | 48 (13.3) | | | |
| CE-PTE | | (N = 284) | (N = 292) | | | |
| | Clinical Success | 278 (97.9) | 279 (95.5) | 2.3 | (−0.6, 5.6) | (−0.5, 5.8) |
| | Clinical Failure | 6 (2.1) | 13 (4.5) | | | |

CI = Confidence Interval; Difference is observed difference in Overall Clinical Success rate at PTE between the omadacycline and linezolid groups.
[1] 95% CI was constructed based on the Miettinen and Nurminen method without stratification.
[2] 95% CI was adjusted for type of infection and receipt of prior antibiotics based on the Miettinen and Nurminen method with stratification, using Cochran-Mantel-Haenszel weights as stratum weights. For [2], the receipt of prior antibiotic subgroups were combined into one group. Infection type was not combined. Overall Clinical Response at PTE was based on the Investigator Assessment at the EOT and PTE visits. Percentages were based on the number of subjects in each treatment group.

The overall clinical success/response rates at PTE visit based on investigator assessment of the mITT PTE population and the CE-PTE population, for both Omadacycline and Linezolid, are also depicted in FIG. 6. See the middle (mITT PTE) and the right most (CE-PTE) pairs of bars. The data shows that the observed 3.3% difference in overall clinical response rate in the mITT PTE population is within the 10% margin of statistical non-inferiority between −2.2% and 9.0% (with stratification), at 95% CI (Confidence Interval); and that the observed 2.3% difference in overall clinical response rate in the CE-PTE population is within the 10% margin of statistical non-inferiority between −0.5% and 5.8% (with stratification), at 95% CI (Confidence Interval). Thus the co-primary efficacy points (for EMA approval) are also met.

Overall clinical response at PTE visit based on investigator assessments by type of infection in the mITT population is summarized below:

| | Type of Infection as Randomized | | | Actual Type of Infection[1] | | |
|---|---|---|---|---|---|---|
| Type of Infection Efficacy Outcome | Omadacycline (N = 360) n (%) | Linezolid (N = 360) n (%) | Difference (95% CI) | Omadacycline (N = 360) n (%) | Linezolid (N = 360) n (%) | Difference (95% CI) |
| Wound Infection | 214 | 214 | | 210 | 214 | |
| Clinical Success | 177 (82.7) | 164 (76.6) | 6.1 (−1.6, 13.7) | 173 (82.4) | 164 (76.6) | 5.7 (−2.0, 13.4) |
| Clinical Failure or Indeterminate | 37 (17.3) | 50 (23.4) | | 37 (17.6) | 50 (23.4) | |
| Clinical Failure | 8 (3.7) | 17 (7.9) | | 8 (3.8) | 17 (7.9) | |
| Indeterminate | 29 (13.6) | 33 (15.4) | | 29 (13.8) | 33 (15.4) | |
| Cellulitis/erysipelas | 82 | 84 | | 86 | 84 | |
| Clinical Success | 72 (87.8) | 78 (92.9) | −5.1 (−14.9, 4.3) | 76 (88.4) | 78 (92.9) | −4.5 (−14.0, 4.7) |
| Clinical Failure or Indeterminate | 10 (12.2) | 6 (7.1) | | 10 (11.6) | 6 (7.1) | |

|  | Type of Infection as Randomized | | | Actual Type of Infection[1] | | |
|---|---|---|---|---|---|---|
| Type of Infection Efficacy Outcome | Omadacycline (N = 360) n (%) | Linezolid (N = 360) n (%) | Difference (95% CI) | Omadacycline (N = 360) n (%) | Linezolid (N = 360) n (%) | Difference (95% CI) |
| Clinical Failure | 2 (2.4) | 1 (1.2) | | 2 (2.3) | 1 (1.2) | |
| Indeterminate | 8 (9.8) | 5 (6.0) | | 8 (9.3) | 5 (6.0) | |
| Major Abscess | 64 | 62 | | 64 | 62 | |
| Clinical Success | 54 (84.4) | 49 (79.0) | 5.3 (−8.4, 19.2) | 54 (84.4) | 49 (79.0) | 5.3 (−8.4, 19.2) |
| Clinical Failure or Indeterminate | 10 (15.6) | 13 (21.0) | | 10 (15.6) | 13 (21.0) | |
| Clinical Failure | 2 (3.1) | 3 (4.8) | | 2 (3.1) | 3 (4.8) | |
| Indeterminate | 8 (12.5) | 10 (16.1) | | 8 (12.5) | 10 (16.1) | |

CI = Confidence Interval; Difference is observed difference in Overall Clinical Success rate at PTE between the omadacycline and linezolid groups. 95% CI within each type of infection was constructed based on the Miettinen and Nurminen method without stratification. Percentages were based on the number of subjects in each treatment group within each type of infection.
[1]Actual type of infection = Type of infection recorded on eCRF.

Overall clinical success at PTE visit based on investigators assessment by baseline pathogen from the ABSSSI site or blood culture micro-mITT population is summarized below:

Additional and sensitivity analyses of the primary efficacy outcomes (Early Clinical Response and Investigator's Assessment of Clinical Response at PTE) were performed (data not shown). Sensitivity analyses included: conducting

|  | Omadacycline (N = 276) | | Linezolid (N = 287) | |
|---|---|---|---|---|
| Baseline Pathogen | N1 | Clinical Success n (%) | N1 | Clinical Success n (%) |
| *Gram-positive organisms (aerobes)* | | | | |
| *Staphylococcus aureus* | 220 | 182 (82.7) | 233 | 186 (79.8) |
| MRSA | 104 | 89 (85.6) | 107 | 85 (79.4) |
| MSSA | 120 | 97 (80.8) | 130 | 103 (79.2) |
| *Staphylococcus lugdunensis* | 5 | 4 (80.0) | 0 | 0 |
| *Streptococcus pyogenes* | 29 | 20 (69.0) | 16 | 9 (56.3) |
| *Streptococcus anginosus group* | 57 | 49 (86.0) | 45 | 33 (73.3) |
| *Streptococcus anginosus* | 27 | 24 (88.9) | 20 | 16 (80.0) |
| *Streptococcus intermedius* | 23 | 18 (78.3) | 24 | 16 (66.7) |
| *Streptococcus constellatus* | 9 | 8 (88.9) | 7 | 5 (71.4) |
| *Enterococcus faecalis* | 8 | 8 (100.0) | 12 | 9 (75.0) |
| VRE | 0 | 0 | 2 | 2 (100.0) |
| VSE | 7 | 7 (100.0) | 10 | 7 (70.0) |
| *Enterococcus faecium* | 1 | 1 (100.0) | 1 | 1 (100.0) |
| VSE | 1 | 1 (100.0) | 1 | 1 (100.0) |
| *Streptococcus agalactiae* | 2 | 1 (50.0) | 2 | 1 (50.0) |
| *Streptococcus mitis* | 1 | 1 (100.0) | 0 | 0 |
| . . . | | | | |
| Streptococcus viridans group | 3 | 3 (100.0) | 20 | 0 |
| *Gram-positive organisms (anaerobes)* | | | | |
| *Clostridium perfringens* | 5 | 4 (80.0) | 9 | 7 (77.8) |
| *Finegoldia magna* | 3 | 3 (100.0) | 1 | 0 (0.0) |
| . . . | | | | |
| *Gram-negative organisms (aerobes)* | | | | |
| *Enterobacter cloacae* | 5 | 4 (80.0) | 6 | 6 (100.0) |
| *Escherichia coli* | 4 | 4 (100.0) | 1 | 1 (100.0) |
| *Klebsiella pneumoniae* | 5 | 4 (80.0) | 6 | 4 (66.7) |
| . . . | | | | |
| *Gram-negative organisms (anaerobes)* | | | | |
| *Prevotella denticola* | 5 | 3 (60.0) | 1 | 0 (0.0) |
| *Prevotella melaninogenica* | 2 | 2 (100.0) | 3 | 3 (100.0) |
| . . . | | | | |

N1 = Number of subjects in the micro-mITT population in the treatment group with the baseline pathogen.
n = Number of subjects in the specific category.

Percentages were based on N1. Subjects with the same pathogen isolated from multiple specimens were counted only once for that pathogen. Subjects with the same pathogen identified from both the blood and primary ABSSSI cultures were counted only once. Percentages were based on the number of subjects in each treatment group having the indicated pathogen.

an adjusted analysis of the primary efficacy outcome based on the randomized stratum and separately, based on the stratum the subject actually belongs, and conducting an analysis where all subjects with an Indeterminate response are considered Clinical Successes.

Secondary Efficacy Analysis

The number and percentage of subjects classified as a Clinical Success, Clinical Failure and Indeterminate by the Investigator's Assessment at PTE in the mITT and CE populations (by definition subjects with an Indeterminate response were excluded from the CE population) were calculated for each treatment group. A 2-sided unadjusted 95% CI was constructed for the observed difference in the clinical success rate using the method of Miettinen and Nurminen. For Investigator's Assessment of Clinical Response at PTE in the mITT and CE populations the 2-sided 95% CI was for descriptive purposes only and no conclusion of NI was made.

The number and percentage of subjects in each treatment group in each response category for Early Clinical Response were presented for the micro-mITT population. The number and percentage of subjects who were classified as a Clinical Success and Clinical Failure by the investigator at the PTE visit in the ME population were calculated. Two-sided unadjusted 95% CI was constructed for the observed difference in the clinical success rates using the method of Miettinen and Nurminen.

The number and percentage of subjects with an Early Clinical Response of success and an Investigator's Assessment of Clinical Response at PTE of Clinical Success by pathogen (including Gram-negative causative pathogens and MRSA) were provided in the micro-mITT and ME populations.

Analysis of Additional Efficacy Variables

Additional efficacy analyses were conducted to support the efficacy findings of the primary and secondary outcomes. CIs were determined for descriptive purposes, but no conclusions of NI were made.

The number and percentage of subjects classified as an Early Clinical Success, Clinical Failure and Indeterminate at 48 to 72 hours after the first dose of test article in the ITT population were calculated. A 2-sided unadjusted 95% CI was constructed for the observed difference in the Clinical Success rate using the method of Miettinen and Nurminen.

The number and percentage of subjects classified as a Clinical Success, Clinical Failure and Indeterminate by the Investigator's Assessment at EOT in the mITT and CE populations (by definition subjects with an Indeterminate response were excluded from the CE population) were calculated for each treatment group. A 2-sided unadjusted 95% CI was constructed for the observed difference in the clinical success rate using the method of Miettinen and Nurminen.

Descriptive summaries, including change from baseline where appropriate, of the clinical signs and symptoms (tenderness, edema, erythema, induration and drainage), complete resolution of the clinical signs and symptoms, temperature, ABSSSI lesion measurements (including absolute and percentage reduction in lesion area, e.g., 0 to <5%, 5 to <10%, 10 to <20%, ≥20%, etc.), and systemic signs by study visit were presented.

All-cause mortality (ACM) at 15 and 30 days after the first dose of test article was summarized in the ITT population. Subjects who were lost to follow-up are considered deceased for this analysis. A 2-sided unadjusted 95% CI for the observed difference in mortality rates was calculated for ACM.

The per-subject and per-pathogen microbiologic outcomes were provided for the micro-mITT and ME populations at the EOT and PTE visits. Two-sided unadjusted 95% CIs were provided for the difference in per-subject microbiological favorable outcome rates.

A concordance analysis of Early Clinical Response and Investigator's Assessment of Clinical Response at PTE in the mITT analysis set were presented.

Safety Outcome Measures

Safety variables include the incidence rate of AEs, change in vital signs, ECG parameters and laboratory test results obtained during the course of the study. For safety analyses, subjects were analyzed according to the treatment actually received.

Summary tables were provided for all treatment-emergent adverse events (TEAEs). A TEAE is defined as an AE with a start date and time on or after the first dose of test article. AEs were coded using the Medical Dictionary for Regulatory Activities (MedDRA) and were summarized by presenting the number and percentage of subjects having each TEAE for each treatment group by system organ class (SOC) and preferred term (PT). Additional tabulations provide summaries by SOC and PT of subjects experiencing SAEs, severe TEAEs, TEAEs judged to be related to test article, TEAEs leading to discontinuation of test article, and TEAEs of special interest.

An overview of the AEs in the safety population is provided below:

| Parameter | Omadacycline (N = 368) n (%) | Linezolid (N = 367) n (%) |
| --- | --- | --- |
| Total Number of AEs | 468 | 250 |
| Total Number of TEAEs | 448 | 239 |
| Subjects with at Least One, n (%) | | |
| Adverse Events (AE) | 201 (54.6) | 140 (38.1) |
| TEAE | 197 (53.5) | 137 (37.3) |
| Drug-Related TEAE | 139 (37.8) | 52 (14.2) |
| Severe TEAE | 6 (1.6) | 7 (1.9) |
| Serious TEAE | 5 (1.4) | 5 (1.4) |
| Drug-Related Serious TEAE | 0 | 1 (0.3) |
| Serious TEAE leading to Death | 0 | 1 (0.3) |
| TEAE leading to premature discontinuation of test article | 6 (1.6) | 3 (0.8) |
| TEAE leading to premature discontinuation of study | 3 (0.8) | 1 (0.3) |
| TEAE leading to dose interruption | 0 | 0 |
| Serious TEAEs leading to premature discontinuation of test article | 3 (0.8) | 2 (0.5) |
| Subjects who died, n (%) | 0 | 1 (0.3) |

Percentages were based on the Safety population. A TEAE is defined as an AE occurring after first dose of active test article.

A summary of treatment-emergent adverse events (TEAEs) leading to study drug discontinuation by system organ class and preferred term in the safety population is provided below:

| System Organ Class (SOC) Preferred Term (PT) | Omadacycline (N = 368) n (%) | Linezolid (N = 367) n (%) |
| --- | --- | --- |
| Subjects with at Least One TEAE Leading to Study Drug Discontinuation | 6 (1.6) | 3 (0.8) |
| Gastrointestinal Disorders | 1 (0.3) | 0 |
| Haematemesis | 1 (0.3) | 0 |
| Nausea | 1 (0.3) | 0 |
| Vomiting | 1 (0.3) | 0 |
| Infections And Infestations | 4 (1.1) | 1 (0.3) |

-continued

| System Organ Class (SOC)<br>Preferred Term (PT) | Omadacycline<br>(N = 368)<br>n (%) | Linezolid<br>(N = 367)<br>n (%) |
|---|---|---|
| Wound Infection | 1 (0.3) | 1 (0.3) |
| Cellulitis | 1 (0.3) | 0 |
| Staphylococcal Bacteraemia | 1 (0.3) | 0 |
| Subcutaneous Abscess | 1 (0.3) | 0 |
| Pregnancy, Puerperium And Perinatal Conditions | 1 (0.3) | 0 |
| Pregnancy | 1 (0.3) | 0 |

Coding of system organ class and preferred term was based on MedDRA Version 17.1. Percentages were based on the Safety population. A TEAE is defined as an AE occurring after first dose of active test article. If a subject had more than one TEAE that coded to the same MedDRA category, the subject was counted only once.

A summary of the most frequent (≥2%) treatment-emergent adverse events (TEAEs) by preferred term in the safety population is provided below:

| Preferred Term (PT) | Omadacycline<br>(N = 368)<br>n (%) | Linezolid<br>(N = 367)<br>n (%) |
|---|---|---|
| Subjects with at Least One TEAE | 197 (53.5) | 137 (37.3) |
| Nausea | 111 (30.2) | 28 (7.6) |
| Vomiting | 62 (16.8) | 11 (3.0) |
| Wound Infection | 22 (6.0) | 17 (4.6) |
| Alanine Aminotransferase Increased | 19 (5.2) | 11 (3.0) |
| Aspartate Aminotransferase Increased | 17 (4.6) | 12 (3.3) |
| Diarrhea | 15 (4.1) | 10 (2.7) |
| Headache | 13 (3.5) | 8 (2.2) |
| Cellulitis | 12 (3.3) | 9 (2.5) |
| Abdominal Pain Upper | 10 (2.7) | 4 (1.1) |
| ... | | |

Coding of preferred term was based on MedDRA Version 17.1. Percentages were based on the safety population. A TEAE was defined as an AE occurring after first dose of active test article. If a subject had more than one TEAE that coded to the same MedDRA category, the subject was counted only once.

A summary of the most frequent GI treatment-emergent adverse events (TEAEs) in the safety population is provided below:

| | Omadacycline (N = 368) | | | Linezolid (N = 367) | | |
|---|---|---|---|---|---|---|
| System Organ Class (SOC)<br>Preferred Term (PT) | Mild<br>n (%) | Moderate<br>n (%) | Severe<br>n (%) | Mild<br>n (%) | Moderate<br>n (%) | Severe<br>n (%) |
| Subjects with at Least One TEAE | 120 (32.6) | 71 (19.3) | 6 (1.6) | 85 (23.2) | 45 (12.3) | 7 (1.9) |
| Gastrointestinal Disorders | 105 (28.5) | 39 (10.6) | 0 | 44 (12.0) | 8 (2.2) | 0 |
| Nausea | 83 (22.6) | 28 (7.6) | 0 | 24 (6.5) | 4 (1.1) | 0 |
| Vomiting | 44 (12.0) | 18 (4.9) | 0 | 10 (2.7) | 1 (0.3) | 0 |
| Abdominal Pain | 3 (0.8) | 3 (0.8) | 0 | 1 (0.3) | 1 (0.3) | 0 |
| Diarrhea | 13 (3.5) | 2 (0.5) | 0 | 9 (2.5) | 1 (0.3) | 0 |
| Abdominal Pain Upper | 9 (2.4) | 1 (0.3) | 0 | 4 (1.1) | 0 | 0 |

Coding of system organ class and preferred term was based on MedDRA Version 17.1. Percentages were based on the Safety population. A TEAE was defined as an AE occurring after first dose of active test article. If a subject had more than one TEAE that coded to the same MedDRA category, the subject was counted only once at the highest severity. TEAEs with missing severity were not displayed.

The following variables were analyzed descriptively: Vital signs (systolic and diastolic BP, pulse rate, body temperature, respiratory rate), including change from Screening by visit; Clinically notable vital signs (meeting predefined criteria as specified in the SAP) by visit. Subjects with notable vital signs data were listed.

ECG data (RR interval, PR interval, QRS interval, QTc, QTc Bazett's Correction Formula [QTcB], and QTc Fridericia's Correction Formula [QTcF]) was summarized descriptively at each scheduled evaluation, and for the overall worst post-Screening value. Changes from Screening at each visit that a 12-lead ECG was obtained was also provided. An outlier analysis was conducted based on the worst post-Screening value.

The following variables were analyzed descriptively: Laboratory variables by visit; Change from Screening of laboratory variables by visit; and Clinically notable laboratory values (meeting predefined criteria specified in the SAP) by visit.

Listings of individual subject laboratory data were generated. Values meeting predefined criteria for being clinically notable were flagged within the listings.

Pharmacokinetics

Population PK analysis was conducted to characterize PK parameters. A population PK data set including subjects with 1 or more quantified omadacycline concentration determinations are constructed from the dates and times of the doses and blood samples along with all the bioanalytical determinations and subject background information. If the actual date or time for a blood sample or dose was missing, the related bioanalytical determination of the PK concentration was excluded from all analyses. Omadacycline concentrations below the limit of quantification were treated as missing data in summary statistics and for the calculation of PK parameters.

Variables including age (years), body weight (kg), gender, and race/ethnicity along with other covariates previously determined to be important were incorporated into the population PK database. Based on the subjects in the population analysis data set, descriptive summaries at Screening for these variables were reported. Outliers may be excluded from the analysis. These were determined by a scatter plot of the observed concentration versus time post dose reported. The distribution of the number of samples contributed per subject to the model-based analysis was tabulated. Also, simple summary descriptive statistics for the concentration of samples by study day or week were computed.

Concerning population PK modeling, results from Phase 1 studies indicated that omadacycline PK was linear and that following intravenous infusion, plasma concentration-time profiles show a 3-compartmental disposition. Therefore, the probable structural PK model would be a 3-compartment model with zero order input for i.v. infusion and first order input for p.o. administration. This PK model contains the parameters clearance, volume of distribution, bioavailability and absorption rate constant. The associated population models are nonlinear mixed-effects models. The population model adds random effects and covariates for the PK parameters in order to recognize differences among individuals and similarities across observations corresponding to the same subject. At the time of the population modeling, previously reported structural PK models will be considered first. A residual error model combining additive error and proportional error is initially considered. Simplifications (e.g., fewer random affects or an alternative residual error model) may be appropriate if the diagnostics for the model suggest false convergence. Additional covariates are investigated graphically (gender, race/ethnicity, age) as part of the model diagnostics and some may be retained in the final model and additional ones in a competing model to deliver estimates of arguably insignificant effects. Scatter plots of the observed concentrations versus population-estimated and individually estimated concentrations are used as part of the overall assessment of the overall quality of the fit. During modeling, the broad principles outlined by the FDA are followed.

The individual model-based exposure measures at steady state (area under the curve $[AUC]_{0-24}$,ss, time to maximum plasma concentration $[T_{max}$,ss], maximum plasma concentration $[C_{max}$,ss]) are computed and summarized.

The relationship between omadacycline exposure and response (efficacy and safety) will be examined as appropriate for the data. A population PK model will be used to calculate individual subject AUCs and, subsequently, possible AUC/MIC breakpoints.

The invention claimed is:

1. A method of treating a human subject in need of treatment for a bacterial skin or skin structure infection, comprising orally administering to said subject an effective amount of 9-[(2,2-dimethyl-propyl amino)-methyl]-minocycline or a salt thereof, such that said subject is treated, wherein said 9-[(2,2-dimethyl-propyl amino)-methyl]-minocycline is administered orally at a dose of about 450 mg per day for two consecutive days, then at a dose of about 300 mg per day for 5 or more days.

2. The method of claim 1, wherein the bacterial skin or skin structure infection is wound infection, cellulitis/erysipelas, major abscess, furuncles/boils, carbuncle, Staphylococcal scalded skin syndrome (SSSS), or ecthyma.

3. The method of claim 1, wherein the bacterial skin or skin structure infection is Acute Bacterial Skin and Skin Structure Infection (ABSSSI).

4. The method of claim 3, wherein the ABSSSI is community-acquired ABSSSI.

5. The method of claim 4, wherein the ABSSSI comprises wound infection, cellulitis/erysipelas, and/or major abscess.

6. The method of claim 1, wherein said bacterial skin or skin structure infection is a result of skin injury including but not limited to trauma, a surgical procedure, or IV drug use.

7. The method of claim 1, wherein said human subject is administered 9-[(2,2-dimethyl-propyl amino)-methyl]-minocycline under fasting condition.

8. The method of claim 1, wherein said 9-[(2,2-dimethyl-propyl amino)-methyl]-minocycline is administered once per day.

9. The method of claim 1, wherein said subject is treated up to and including about 14 days, up to and including about 10 days, up to and including about 9 days, up to and including about 8 days, or up to and including about 7 days, up to and including about 5 days, such that said subject is treated.

10. The method of claim 9, wherein said subject is treated for 7-10 days.

11. The method of claim 1, wherein said salt is a tosylate salt.

12. The method of claim 1, wherein said bacterial skin or skin structure infection is known or suspected to be caused by Gram-positive pathogens selected from the group consisting of: *Staphylococcus aureus, Staphylococcus lugdunensis, Streptococcus species, Streptococcus agalactiae, Streptococcus mitis, Enterococcus* species (*Enterococcus faecalis* (such as VRE or VSE), or *Enterococcus faecium* (such as VRE or VSE)), *Streptococcus anginosus* group (*S. anginosus, S. constellatus*, and *S. intermedius*, that is beta-, alpha- or non-hemolytic), *Viridans* group Streptococci (VGS), *Clostridium perfringens, Finegoldia magna*, and a combination thereof.

13. The method of claim 12, wherein:
(a) said *Staphylococcus aureus* is methicillin-resistant *Staphylococcus aureus* (MRSA), or methicillin-susceptible *Staphylococcus aureus* (MSSA);
(b) said *Streptococcus* species include *Streptococcus anginosus* group;
(c) said *Streptococcus* species include beta-hemolytic Streptococci or *S. anginosus;*
(d) said *Streptococcus* species include non-hemolytic Streptococci or *S. intermedius;*
(e) said *Streptococcus* species include alpha-hemolytic Streptococci or *S. constellatus;*
(f) said *Enterococcus* species include *Enterococcus faecalis* (VSE); or,
(g) said *Streptococcus* species include *Streptococcus pyogenes.*

14. The method of claim 1, wherein said bacterial skin or skin structure infection is known or suspected to be caused by Gram-negative pathogens selected from the group consisting of: *Enterobacter cloacae, Escherichia coli, Klebsiella pneumoniae, Prevotella denticola, Prevotella melaninogenica*, and a combination thereof.

15. The method of claim 1, wherein GI adverse events (AEs) associated with treatment are predominantly mild, or do not result in discontinuation of therapy.

16. The method of claim 1, wherein Area Under the Curve from 0-24 hours ($AUC_{0-24}$) after the first two doses of 9-[(2,2-dimethyl-propyl amino)-methyl]-minocycline or a salt thereof is about 10,000 ng*h/mL.

17. The method of claim 1, wherein each dose of said 9-[(2,2-dimethyl-propyl amino)-methyl]-minocycline or salt thereof is administered as 150 mg tablets.

* * * * *